US011744998B2

(12) United States Patent
Lee

(10) Patent No.: US 11,744,998 B2
(45) Date of Patent: Sep. 5, 2023

(54) DRUG DELIVERY DEVICES WITH DRUG-PERMEABLE COMPONENT AND METHODS

(71) Applicant: TARIS Biomedical LLC, Lexington, MA (US)

(72) Inventor: Heejin Lee, Bedford, MA (US)

(73) Assignee: TARIS Biomedical LLC, Lexington, MA (US)

( * ) Notice: Subject to any disclaimer, the term of this patent is extended or adjusted under 35 U.S.C. 154(b) by 282 days.

(21) Appl. No.: 17/139,085

(22) Filed: Dec. 31, 2020

(65) Prior Publication Data

US 2021/0121670 A1     Apr. 29, 2021

Related U.S. Application Data

(62) Division of application No. 15/137,837, filed on Apr. 25, 2016, now Pat. No. 10,894,150.

(Continued)

(51) Int. Cl.
*A61M 31/00* (2006.01)
*A61J 1/00* (2023.01)
(Continued)

(52) U.S. Cl.
CPC .............. *A61M 31/002* (2013.01); *A61J 1/00* (2013.01); *A61J 1/03* (2013.01); *A61K 9/0034* (2013.01); *A61K 9/20* (2013.01); *A61K 45/06* (2013.01); *A61L 31/06* (2013.01); *A61L 31/14* (2013.01); *A61L 31/16* (2013.01); *A61M 2207/00* (2013.01); *A61M 2210/1085* (2013.01);

(Continued)

(58) Field of Classification Search
CPC ........ A61K 9/0034; A61M 2210/1085; A61M 31/002
See application file for complete search history.

(56) References Cited

U.S. PATENT DOCUMENTS

| 2,118,631 A | 10/1971 | Wappler |
| 3,786,813 A | 1/1974 | Michaels |

(Continued)

FOREIGN PATENT DOCUMENTS

| DE | 3332156 | 3/1985 |
| EP | 0572932 | 9/2000 |

(Continued)

OTHER PUBLICATIONS

Appell, Rodeney A. et al., "339—A Novel Intravesical Device for Optional Drug Delivery," The Journal of Urology, vol. 163, No. 4, Supplement, Sunday, Apr. 30, 2000, pp. 77.

(Continued)

*Primary Examiner* — Deanna K Hall
(74) *Attorney, Agent, or Firm* — Eversheds Sutherland (US) LLP

(57) ABSTRACT

Drug delivery devices having a drug-permeable component and methods of making and using the same are provided. Drug delivery devices include a housing having a first and second wall structures that are adjacent one another and together form a tube defining a drug reservoir lumen. The second wall structure, or both the first wall structure and the second wall structure, are permeable to water, and the first wall structure is impermeable to the drug while the second wall structure is permeable to the drug, such that the drug is releasable in vivo by diffusion through the second wall structure.

20 Claims, 8 Drawing Sheets

Related U.S. Application Data

(60) Provisional application No. 62/293,232, filed on Feb. 9, 2016, provisional application No. 62/151,982, filed on Apr. 23, 2015.

(51) Int. Cl.

| | |
|---|---|
| *A61L 31/16* | (2006.01) |
| *A61J 1/03* | (2023.01) |
| *A61K 9/00* | (2006.01) |
| *A61K 9/20* | (2006.01) |
| *A61K 45/06* | (2006.01) |
| *A61L 31/06* | (2006.01) |
| *A61L 31/14* | (2006.01) |
| *B29C 48/11* | (2019.01) |
| *B29C 48/21* | (2019.01) |
| *B29C 48/00* | (2019.01) |
| *B29K 105/00* | (2006.01) |
| *B29C 48/09* | (2019.01) |
| *B29C 48/19* | (2019.01) |
| *B29K 75/00* | (2006.01) |
| *B29L 31/00* | (2006.01) |

(52) U.S. Cl.
CPC .......... *B29C 48/0022* (2019.02); *B29C 48/09* (2019.02); *B29C 48/11* (2019.02); *B29C 48/19* (2019.02); *B29C 48/21* (2019.02); *B29C 2793/009* (2013.01); *B29K 2075/00* (2013.01); *B29K 2105/0035* (2013.01); *B29K 2995/0092* (2013.01); *B29L 2031/753* (2013.01)

(56) References Cited

U.S. PATENT DOCUMENTS

| | | |
|---|---|---|
| 3,852,833 A | 12/1974 | Koneke et al. |
| 3,854,480 A | 12/1974 | Zaffaroni |
| 3,888,975 A | 6/1975 | Ramwell |
| 3,901,232 A | 8/1975 | Michaels et al. |
| 3,935,860 A | 2/1976 | Hoff |
| 4,016,251 A | 4/1977 | Higuchi et al. |
| 4,210,670 A | 7/1980 | Cooke |
| 4,235,236 A | 11/1980 | Theeuwes |
| 4,392,848 A | 7/1983 | Lucas et al. |
| 4,449,980 A | 5/1984 | Millar et al. |
| 4,475,916 A | 10/1984 | Himmelstein |
| 4,605,412 A | 8/1986 | La Forest et al. |
| 4,629,449 A | 10/1986 | Wong |
| 4,655,219 A | 4/1987 | Petruzzi |
| 4,655,766 A | 4/1987 | Theeuwes et al. |
| 4,678,463 A | 7/1987 | Millar |
| 4,826,501 A | 5/1989 | Grundei |
| 4,871,542 A | 10/1989 | Vilhardt |
| 4,940,465 A | 7/1990 | Theeuwes et al. |
| 4,955,858 A | 9/1990 | Drews |
| 4,968,507 A | 11/1990 | Zenter et al. |
| 5,005,591 A | 4/1991 | Austud |
| 5,062,829 A | 11/1991 | Pryor et al. |
| 5,146,933 A | 9/1992 | Boyd |
| 5,366,738 A | 11/1994 | Rork et al. |
| 5,441,550 A | 8/1995 | Hassenboehler, Jr. et al. |
| 5,499,997 A | 3/1996 | Sharpe et al. |
| 5,516,522 A | 5/1996 | Peyman et al. |
| 5,551,954 A | 9/1996 | Buscemi et al. |
| 5,629,008 A | 5/1997 | Lee |
| 5,630,843 A | 5/1997 | Rosenberg |
| 5,697,974 A | 12/1997 | Wang |
| 5,700,288 A | 12/1997 | Eaton |
| 5,709,874 A | 1/1998 | Hanson et al. |
| 5,788,980 A | 8/1998 | Nabhi |
| 5,795,591 A | 8/1998 | Lee et al. |
| 5,797,898 A | 8/1998 | Santini, Jr. et al. |
| 5,830,230 A | 11/1998 | Breyman et al. |
| 5,851,217 A | 12/1998 | Wolff et al. |
| 5,855,906 A | 1/1999 | McClay |
| 5,869,081 A | 2/1999 | Jackanicz et al. |
| 5,972,372 A | 10/1999 | Saleh et al. |
| 5,989,581 A | 11/1999 | Groenwegen |
| 5,997,574 A | 12/1999 | Hayes et al. |
| 6,039,967 A | 3/2000 | Ottoboni et al. |
| 6,039,968 A | 3/2000 | Nabhi |
| 6,083,933 A | 7/2000 | Hahn |
| 6,086,909 A | 7/2000 | Harrison et al. |
| 6,139,535 A | 10/2000 | Greelis et al. |
| 6,171,298 B1 | 1/2001 | Matsuura et al. |
| 6,183,461 B1 | 2/2001 | Matsuura et al. |
| 6,207,180 B1 | 3/2001 | Ottoboni et al. |
| 6,283,998 B1 | 9/2001 | Eaton |
| 6,293,923 B1 | 9/2001 | Yachia et al. |
| 6,368,356 B1 | 4/2002 | Zhong et al. |
| 6,398,718 B1 | 6/2002 | Yachia et al. |
| 6,398,757 B1 | 6/2002 | Vareene et al. |
| 6,416,780 B1 | 7/2002 | Passmore et al. |
| 6,419,690 B1 | 7/2002 | Mikus et al. |
| 6,444,224 B1 | 9/2002 | Rathbone et al. |
| 6,464,999 B1 | 10/2002 | Huo et al. |
| 6,482,837 B1 | 11/2002 | Wood |
| 6,491,666 B1 | 12/2002 | Santini, Jr. et al. |
| 6,524,608 B2 | 2/2003 | Ottoboni et al. |
| 6,537,193 B1 | 3/2003 | Lennox |
| 6,656,162 B2 | 12/2003 | Santini, Jr. et al. |
| 6,682,473 B1 | 1/2004 | Matsuura et al. |
| 6,695,830 B2 | 2/2004 | Vigil et al. |
| 6,712,784 B2 | 3/2004 | Huang |
| 6,730,072 B2 | 5/2004 | Shawgo et al. |
| 6,746,421 B2 | 6/2004 | Yachia et al. |
| 6,749,617 B1 | 6/2004 | Palasis et al. |
| 6,753,011 B2 | 6/2004 | Faour |
| 6,808,522 B2 | 10/2004 | Richards et al. |
| 6,875,208 B2 | 4/2005 | Santini, Jr. et al. |
| 6,899,890 B2 | 5/2005 | Kirschner et al. |
| 6,932,810 B2 | 8/2005 | Ryan |
| 6,949,125 B2 | 9/2005 | Robertson |
| 6,951,654 B2 | 10/2005 | Malcolm et al. |
| 6,973,718 B2 | 12/2005 | Sheppard, Jr. et al. |
| 6,976,950 B2 | 12/2005 | Connors et al. |
| 6,976,951 B2 | 12/2005 | Connors et al. |
| 6,988,983 B2 | 1/2006 | Connors et al. |
| 6,996,433 B2 | 2/2006 | Burbank et al. |
| 7,005,138 B2 | 2/2006 | Mahashabde et al. |
| 7,066,914 B2 | 6/2006 | Andersen |
| 7,074,178 B2 | 11/2006 | Connors et al. |
| 7,232,421 B1 | 6/2007 | Gambale et al. |
| 7,521,064 B2 | 4/2009 | Saxena et al. |
| 7,647,112 B2 | 1/2010 | Tracey et al. |
| 7,842,303 B2 | 11/2010 | Kuo et al. |
| 7,858,110 B2 | 12/2010 | Kuzma et al. |
| 7,862,552 B2 | 1/2011 | McIntyre et al. |
| 7,879,088 B2 | 2/2011 | Gao et al. |
| 8,167,836 B2 | 5/2012 | Lee et al. |
| 8,182,464 B2 | 5/2012 | Lee et al. |
| 8,303,977 B2 | 11/2012 | Kuzma et al. |
| 8,343,516 B2 | 1/2013 | Daniel et al. |
| 8,343,528 B2 | 1/2013 | Kuo et al. |
| 8,357,389 B2 | 1/2013 | Kuo et al. |
| 8,460,274 B2 | 9/2013 | Kuzma et al. |
| 8,529,936 B2 | 9/2013 | Kuo et al. |
| 8,658,195 B2 | 2/2014 | Kuo et al. |
| 8,690,840 B2 | 4/2014 | Lee et al. |
| 8,784,865 B2 | 7/2014 | Kuzma et al. |
| 8,801,694 B2 | 8/2014 | Lee et al. |
| 2001/0004709 A1 | 6/2001 | Dubrul |
| 2001/0041936 A1 | 11/2001 | Corbitt, Jr. et al. |
| 2002/0068897 A1 | 6/2002 | Jenkins et al. |
| 2002/0164734 A1 | 11/2002 | Jackson et al. |
| 2002/0183265 A1 | 12/2002 | Vogt et al. |
| 2003/0015203 A1 | 1/2003 | Makower et al. |
| 2003/0059456 A1 | 3/2003 | Malcolm et al. |
| 2003/0077310 A1 | 4/2003 | Pathak et al. |
| 2003/0118692 A1 | 6/2003 | Wang et al. |
| 2003/0118649 A1 | 7/2003 | Gao et al. |
| 2003/0139800 A1 | 7/2003 | Campbell |
| 2003/0144734 A1 | 7/2003 | Dreschnack et al. |

(56) References Cited

U.S. PATENT DOCUMENTS

| | | |
|---|---|---|
| 2003/0147936 A1 | 8/2003 | Sahadevan |
| 2003/0229263 A1 | 12/2003 | Connors et al. |
| 2004/0013702 A1 | 1/2004 | Glover |
| 2004/0022824 A1 | 2/2004 | Li et al. |
| 2004/0034332 A1 | 2/2004 | Uhland |
| 2004/0037318 A1 | 2/2004 | Salin et al. |
| 2004/0149294 A1 | 8/2004 | Gianchandani et al. |
| 2004/0220552 A1 | 11/2004 | Heruth et al. |
| 2004/0260272 A1 | 12/2004 | Friedman et al. |
| 2005/0228482 A1 | 10/2005 | Herzog et al. |
| 2005/0234013 A1 | 10/2005 | Parsons |
| 2005/0234431 A1 | 10/2005 | Williams et al. |
| 2005/0238733 A1 | 10/2005 | Henry |
| 2005/0251108 A1 | 11/2005 | Frassica |
| 2005/0273164 A1 | 12/2005 | Bowman et al. |
| 2006/0105010 A1 | 5/2006 | Rahe et al. |
| 2006/0122689 A1 | 6/2006 | Kocur et al. |
| 2006/0217656 A1 | 9/2006 | Freyman et al. |
| 2006/0234978 A1 | 10/2006 | Marcum |
| 2006/0259118 A1 | 11/2006 | Pal et al. |
| 2006/0264897 A1 | 11/2006 | Lobl et al. |
| 2006/0264912 A1 | 11/2006 | McIntyre et al. |
| 2007/0172507 A1 | 7/2007 | Zupkas et al. |
| 2007/0172508 A1 | 7/2007 | Zupkas et al. |
| 2007/0196423 A1 | 8/2007 | Ruane |
| 2007/0254014 A1 | 11/2007 | Ahmed et al. |
| 2007/0255222 A1 | 11/2007 | Li et al. |
| 2007/0275035 A1 | 11/2007 | Herman et al. |
| 2008/0004578 A1 | 1/2008 | Hixon et al. |
| 2008/0051740 A1 | 2/2008 | Sokal et al. |
| 2008/0119729 A1 | 5/2008 | Copa et al. |
| 2008/0234659 A1 | 9/2008 | Cheng et al. |
| 2008/0312636 A1 | 12/2008 | Miller et al. |
| 2009/0004246 A1 | 1/2009 | Woolfson et al. |
| 2009/0149833 A1 | 6/2009 | Cima et al. |
| 2009/0171465 A1 | 7/2009 | Bucay-Couto et al. |
| 2009/0187254 A1 | 7/2009 | Deal et al. |
| 2009/0202608 A1 | 8/2009 | Alessi et al. |
| 2009/0208540 A1 | 8/2009 | Kuzma |
| 2009/0247992 A1 | 10/2009 | Shalon et al. |
| 2009/0292237 A1 | 11/2009 | Overstreet et al. |
| 2010/0003297 A1 | 1/2010 | Tobias et al. |
| 2010/0010627 A1 | 1/2010 | Matheny |
| 2010/0060309 A1 | 3/2010 | Lewis |
| 2010/0076261 A1 | 3/2010 | Neeman et al. |
| 2010/0080835 A1 | 4/2010 | Kuzma |
| 2010/0119694 A1 | 5/2010 | Guo et al. |
| 2010/0145467 A1 | 6/2010 | Davoudi et al. |
| 2010/0152704 A1 | 6/2010 | Lee et al. |
| 2010/0330149 A1 | 12/2010 | Daniel et al. |
| 2010/0331770 A1 | 12/2010 | Lee et al. |
| 2011/0060309 A1 | 3/2011 | Lee et al. |
| 2011/0106006 A1 | 5/2011 | Martin et al. |
| 2011/0106248 A1 | 5/2011 | Kokott et al. |
| 2011/0112475 A1 | 5/2011 | Benson |
| 2011/0137244 A1 | 6/2011 | Lee et al. |
| 2011/0152839 A1 | 6/2011 | Cima et al. |
| 2011/0202036 A1 | 8/2011 | Boyko et al. |
| 2011/0218488 A1 | 9/2011 | Boyoko et al. |
| 2011/0236456 A1 | 9/2011 | Kuzma |
| 2011/0244015 A1 | 10/2011 | Kuzma |
| 2012/0089121 A1 | 4/2012 | Lee et al. |
| 2012/0089122 A1 | 4/2012 | Lee et al. |
| 2012/0191068 A1 | 7/2012 | Himes et al. |
| 2012/0203203 A1 | 8/2012 | Lee et al. |
| 2013/0131637 A1 | 5/2013 | DiCesare |
| 2013/0158675 A1 | 6/2013 | Hutchins, III et al. |
| 2013/0302397 A1 | 11/2013 | Kuzma |
| 2014/0012222 A1 | 1/2014 | Kuzma |
| 2014/0276636 A1 | 9/2014 | Lee et al. |

FOREIGN PATENT DOCUMENTS

| | | |
|---|---|---|
| WO | 95/33511 | 12/1995 |
| WO | 97/44021 | 11/1997 |
| WO | 98/31415 | 7/1998 |
| WO | 99/18884 | 4/1999 |
| WO | 00/40234 | 7/2000 |
| WO | 01/67991 | 9/2001 |
| WO | 02/05800 | 6/2002 |
| WO | 02/085428 | 10/2002 |
| WO | 03/009882 | 2/2003 |
| WO | 03/024357 | 3/2003 |
| WO | 02/00203 | 10/2003 |
| WO | 2004037318 | 7/2004 |
| WO | 2005032524 | 4/2005 |
| WO | 2005072751 | 8/2005 |
| WO | 2005115245 | 12/2005 |
| WO | 2006/121969 | 11/2006 |
| WO | 2007115259 | 10/2007 |
| WO | 2008051889 | 5/2008 |
| WO | 2008115536 | 2/2009 |
| WO | 2008/038281 | 5/2009 |
| WO | 2009029958 | 6/2009 |
| WO | 2010/105093 | 9/2010 |
| WO | 2012/019155 | 2/2012 |
| WO | 2015/026813 A1 | 2/2015 |

OTHER PUBLICATIONS

Berman, et al., "Lidocaine Permeability in Silicone Tissue Expanders: An in Vitro Analysis," Plastic and Reconstructive Surgery; 84(4) (Oct. 1989), pp. 621-623.

Grayson, et al., Molecular release from a polymeric microreservoir device: Influence of chemistry, polymer swelling, and loading on device performance, J. Biomed Mat Res, vol. 69A, No. 3 (2004), pp. 502-512.

McGuire, et al., "In Vivo Diffusion of Lidocaine Through Tissue Expanders," Plastic and Reconstructive Surgery, 89(4):675-678, 1992.

Sconzo, et al. "In Vitro Diffusion of Lidocaine across Endotracheal Tube Cuffs," Regional Anesthesia, (Jan.-Feb. 1990), pp. 37-40.

Woolfson, et al., "Design of a Silicone Reservoir Intravaginal Ring for the Delivery of Oxybutynin," Journal of Controlled Release, 2003, pp. 465-476, vol. 61, Elsevier Science B.V.

Guarracino, F., "On the analysis of cylindrical tubes under flexure: theoretical formulations, experimental data and finite element analyses," Thin-Walled Structures 41, 2003, pp. 127-147.

Qi, et al., "Stress-strain behavior of thermoplastic polyurethanes," Mechanics of Materials, 37, 2005, pp. 817-839.

International Search Report and Written Opinion for International Application No. PCT/US2016/029204, dated Jul. 29, 2016 (24 pages).

DRUG DELIVERY DEVICES WITH DRUG-PERMEABLE COMPONENT AND METHODS

CROSS-REFERENCE TO RELATED APPLICATIONS

This application is divisional of U.S. application Ser. No. 15/137,837, filed Apr. 25, 2016, which claims priority to U.S. Provisional Application No. 62/151,982, filed Apr. 23, 2015 and to U.S. Provisional Application No. 62/293,232, filed Feb. 9, 2016, all of which are incorporated herein by reference.

BACKGROUND

The present disclosure is generally in the field of medical devices, and more particularly relates to drug delivery devices for insertion into the body of patient for controlled release of drug, including but not limited to devices deployable in the urinary bladder for administration of drug into the bladder.

Intravesical drug delivery devices are known. Examples of such devices are described in U.S. Pat. No. 8,679,094 to Cima et al., U.S. Pat. No. 9,017,312 to Lee et al., U.S. Pat. No. 9,107,816 to Lee et al., and U.S. Patent Application Publication No. 2012/0089121 A1 to Lee et al. In some embodiments, the intravesical devices include a water permeable housing defining a drug reservoir lumen which contains a solid or semi-solid drug formulation, and release of the drug in vivo occurs by water from the bladder diffusing into drug reservoir lumen to solubilize the drug, and then an osmotic pressure build-up in the drug reservoir lumen drives the solubilized drug out of the device through a release aperture.

In some cases, e.g., with certain drugs and therapeutic applications, it would be desirable to extend the period over which a therapeutic amount of the drug is released and/or to keep the drug from coming out too quickly. One way of accomplishing this is by retarding the rate at which the water can enter the drug reservoir. U.S. Patent Application Publication No. 2009/0149822 A1 to Cima et al. discloses adding a conformal coating or sheath over at least a portion of an outer surface of the housing to reduce the water-permeability of the housing. However, this approach complicates manufacturing. Furthermore, because the device housing of these intravesical devices typically are designed to be elastically deformable, maintaining an effective coating may be challenging, since the coating may delaminate and/or crack during device deformation, which could undesirably alter the drug release kinetics and negatively impact reproducibility of results.

U.S. Patent Application Publication No. 2014/0276636 A1 to Lee et al. discloses devices in which drug is released from a housing made of a first wall structure and a hydrophilic second wall structure, wherein the first wall structure is impermeable to the drug and the second wall structure is permeable to the drug. It would be desirable to provide improvements and/or alternative embodiments to these devices, to provide devices capable of delivering drugs at effective release rates for a range of different drugs, and to provide methods for making these devices with greater flexibility of and control over the relative sizes and locations of the two wall structures.

SUMMARY

In a first aspect, a drug delivery device includes a housing having a first wall structure and a second wall structure that are adjacent one another and together form a tube defining a drug reservoir lumen, and a drug contained in the drug reservoir lumen. The second wall structure, or both the first wall structure and the second wall structure, are permeable to water, and the first wall structure is impermeable to the drug and the second wall structure is permeable to the drug, such that the drug is releasable in vivo by diffusion through the second wall structure. The second wall structure occupies less than 90 percent of a cross sectional area of the tube, in a cross section normal to the longitudinal axis of the tube, and the first wall structure contains a first polyurethane composition.

In a second aspect, a drug delivery device includes an elongated, elastic housing having a drug reservoir lumen extending between a first closed end and a second closed end, and a drug contained in the drug reservoir lumen. The housing includes a tubular wall structure that is formed of a first annular segment formed entirely of a first material which is impermeable to the drug, and a second annular segment formed at least partially of a second material which is permeable to the drug and configured to release the drug in vivo by diffusion through the second material in the second annular segment. The first annular segment has a first end which is integrally formed and connected with a first end of the second annular segment.

In a third aspect, a drug delivery device includes a tubular housing having a closed drug reservoir lumen bounded by a wall structure containing at least one thermoplastic material, and a drug contained in the drug reservoir lumen. At least a portion of the wall structure is water permeable and at least a portion of the wall structure is permeable to the drug such that the drug is releasable in vivo by diffusion through the drug permeable portion of the wall structure. The tubular housing is elastically deformable from a coiled retention shape suited to retain the device within the urinary bladder of a patient to an uncoiled shape suited for insertion of the device through the patient's urethra and into the bladder, and the tubular housing is thermally shape set to have the coiled retention shape.

In a fourth aspect, a method of making a drug delivery device having an elongated, elastic housing having a drug reservoir lumen extending between a first end and a second end, includes (i) forming a first annular segment entirely of a first material, which is impermeable to a drug to be delivered, by an extrusion process which includes introducing the first material into an extrusion stream, and (ii) forming a second annular segment at least partially of a second material, which is permeable to the drug to be delivered, by intermittently introducing the second material into the extrusion stream with the first material and at preselected positions, effective to form a tubular structure having one or more first annular segments integrally connected to one or more second annular segments.

In a fifth aspect, a method of administering a drug to a patient in need thereof includes inserting into the patient a device including (i) a housing having a first wall structure and a second wall structure that are adjacent one another and together form a tube defining a drug reservoir lumen, and (ii) a drug contained in the drug reservoir lumen, wherein the first wall structure is impermeable to the drug and contains a polyurethane, the second wall structure is permeable to the drug and occupies less than 90 percent of the external surface area of the tube, and wherein the second wall structure, or both the first wall structure and the second wall structure, are permeable to water. The method further includes permitting water to be imbibed through only the second wall structure or through both the first and second wall structures to solubilize the drug, and permitting the solubilized drug to be released from the device by diffusion through the second wall structure.

In a sixth aspect, a method of administering a drug to a patient in need thereof includes inserting into the patient a device including (i) an elongated, elastic housing having a tubular wall structure and a drug reservoir lumen extending between a first closed end and a second closed end, and (ii) a drug contained in the drug reservoir lumen, wherein the wall structure includes a first annular segment formed entirely of a first material which is impermeable to the drug and a second annular segment formed at least partially of a second material which is permeable to the drug, the first annular segment having a first end which is integrally formed and connected with a first end of the second annular segment. The method further includes permitting water to be imbibed through the tubular wall structure to solubilize the drug, and permitting the solubilized drug to be released from the device by diffusion through the second annular segment of the tubular wall structure.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale.

DETAILED DESCRIPTION

Improved implantable drug delivery devices, methods of manufacturing the same, and methods of drug delivery are provided. In a particular embodiment, devices are configured for intravesical insertion and sustained drug delivery, preferably providing a zero order release rate of therapeutically effective amounts of the drug.

Diffusion-Based Drug Delivery Devices

It was discovered that it may be difficult to achieve a zero order release rate beyond three to four days with osmotic pressure delivery mechanisms for certain drugs. In experiments, after three to four days, the drug release rate quickly decreased, which can cause the drug urine concentration in the bladder to fall below a minimum effective concentration before the end of treatment period. It is not always feasible to extend the period of zero order release simply by providing more, or more densely packed, osmotic agent with the drugs, for example due to overall implant system size limitations. It is also not always feasible to instead provide overall first order drug release during an entire treatment period, because it may not be safe to have the initial peak drug release rate high enough that even with the decay of the drug release rate toward the end of the treatment period, the release rate is still above minimum effective concentration of the drug.

Accordingly, the particular devices described herein have been developed, wherein instead of an osmotic drug release mechanism, drug release is controlled by drug diffusion through a drug-permeable polymer or matrix component defining part of the device housing. In one embodiment, the device includes a drug-permeable polymer component or portion. For example, the drug-permeable component or portion of the device may be a portion of the housing formed of a material distinct from the remaining portion of housing (e.g., a strip or multiple strips of material extending along at least a portion of the length of the housing), such that the size, shape (e.g., arc angle), thickness, and material properties of the drug-permeable wall structure may be selected to achieve the desired drug release rate. In certain embodiments, the drug permeable portion, the drug impermeable portion, or both the drug permeable and impermeable portions are formed of polyurethane compositions, to advantageously provide (i) controlled diffusion of the drug from the device, (ii) desired mechanical properties (e.g., compliancy), (iii) a device that may be thermally shape set to have a desired retention shape, and/or (iv) a device which may advantageously be manufactured in a coextrusion process.

Figure 1A:
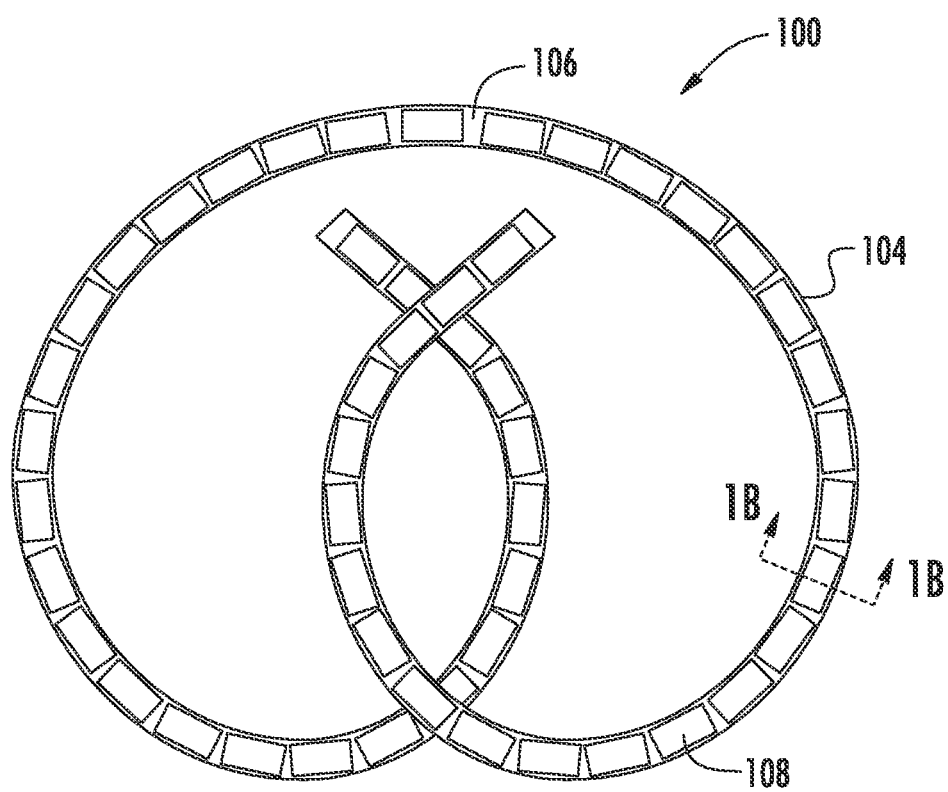
FIG. 1A is a longitudinal cross-sectional view of one embodiment of a drug delivery device in a coiled retention shape, in accordance with the present disclosure.
Figure 1B:
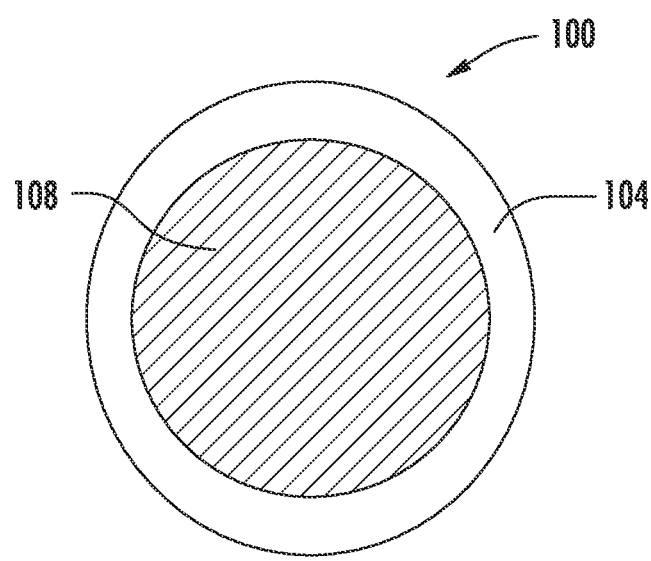
FIG. 1B is a traverse cross-sectional view of the drug delivery device of FIG. 1A, in accordance with the present disclosure.

In one aspect, as shown in FIGS. 1A and 1B, a drug delivery device 100 is provided that includes a tubular housing having a closed drug reservoir lumen 106 bounded by a wall structure 104, wherein (i) at least a portion of the wall structure 104 is water permeable, and (ii) at least a portion of the wall structure is permeable to the drug (contained in solid drug unit 108) such that the drug is releasable in vivo by diffusion through the drug permeable portion of the wall structure 104. In certain embodiments, as discussed in further detail below, the wall structure includes first and second wall structures that together form the housing. As used herein, the phrase "diffusion through the drug permeable portion" (e.g., through the "second wall structure," the "second annular segment," or another "drug permeable portion") refers to the drug being released by passing through the wall by molecular diffusion, and not by passing through an aperture or open structure extending through that wall.

Figure 2:
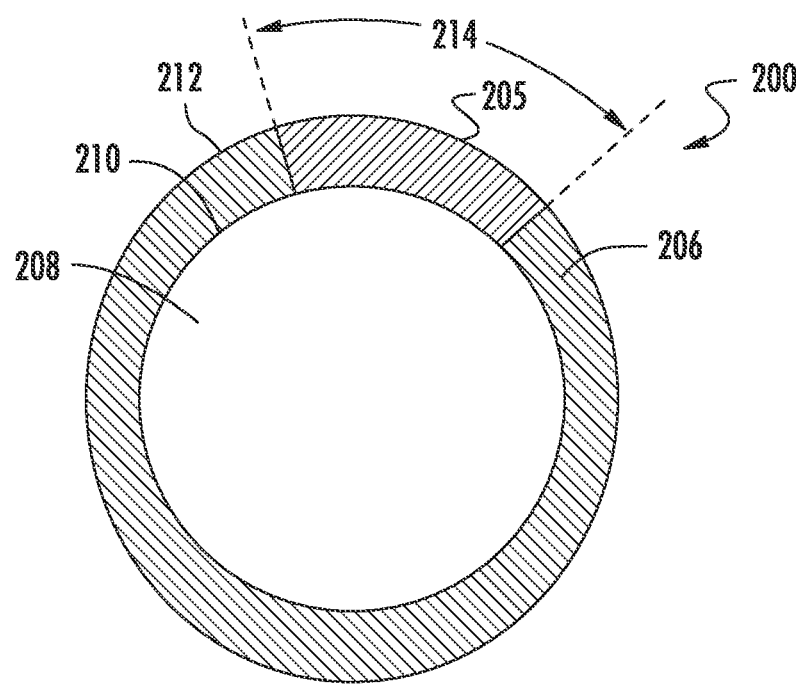
FIG. 2 is a traverse cross-sectional view of one embodiment of a drug delivery device, in accordance with the present disclosure.

In one aspect, as shown in FIG. 2, a drug delivery device 200 is provided that includes a housing with a first wall structure 206 and a second wall structure 205 that are adjacent one another and together form a tube defining a drug reservoir lumen 208, wherein (i) the second wall structure 205, or both the first wall structure 206 and the second wall structure 205, are permeable to water, and (ii) the first wall structure 206 is impermeable to the drug and the second wall structure 205 is permeable to the drug, such that the drug is releasable in vivo by diffusion through the second wall structure 205. As used herein, the term "impermeable to the drug" refers to the wall being substantially impermeable to the solubilized drug, such that no substantial amount of the solubilized drug can diffuse therethrough over the therapeutic period in which the device is located in vivo.

In certain embodiments, the tube is cylindrical or another suitable shape or design. As used herein, the term "cylindrical," when used in reference to the tubular housing, refers to the housing having a substantially cylindrical outer wall. In one embodiment, the device does not include an aperture; drug release is only by diffusion through the second wall structure.

Figure 3:
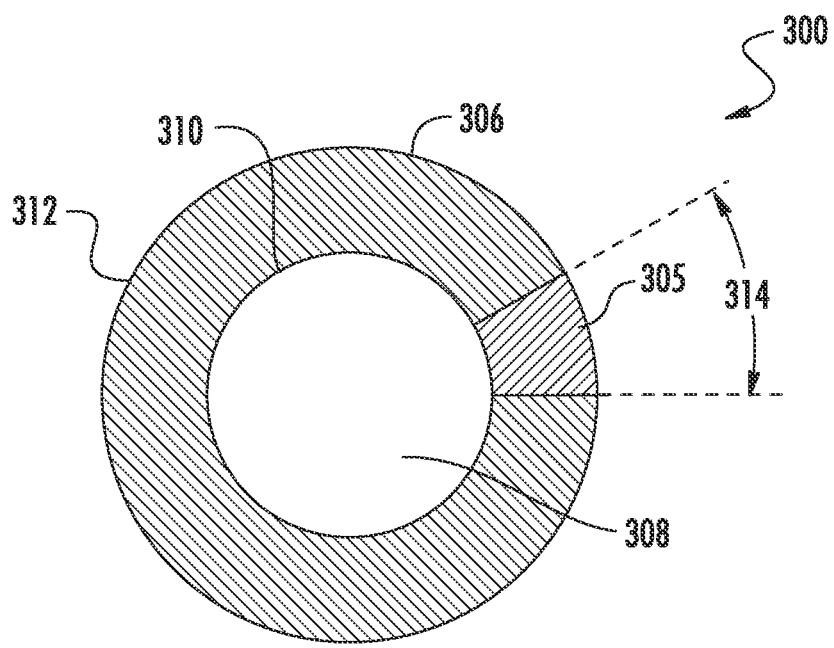
FIG. 3 is a traverse cross-sectional view of one embodiment of a drug delivery device, in accordance with the present disclosure.

In some embodiments, as shown in FIGS. 2 and 3, the first wall structure 206/306 and the second wall structure 205/305 are adjacent one another and together form a cylindrical tube. For example, such devices may be formed in a coextrusion process, such that the first and second wall structures are integrally formed. In one embodiment, the coextruded first and second wall structures are thermoplastic polymers possessing the desired properties.

As shown in FIG. 3, the first wall structure 306 and second wall structure 306 together form a cylindrical tube having a lumen 308 in which a drug formulation is contained. The second wall structure 305 is in the form of a strip extending along at least a portion of the length of the first wall structure 306 and is permeable to the drug, while the first wall structure 306 is not permeable to the drug. In certain embodiments, multiple drug permeable strips may be used in a single device. Thus, the size, shape, thickness, and material properties of the second wall structure may be selected to achieve a desired drug release rate.

In a preferred embodiment, as discussed in further detail below, the device is elastically deformable between a relatively straightened shape suited for insertion through the urethra of a patient and into the patient's bladder and a retention shape suited to retain the device within the bladder. In one embodiment, as shown in FIGS. 7A-7C, 8A-8D, and 10A-10D, the device further includes retention frame lumen 734, 834, 1034. In certain embodiments, the retention frame lumen includes an elastic wire, such a nitinol wire. In certain other embodiments, the retention frame lumen is filled with a shape set elastic polymer. In other embodiments, as shown in FIGS. 1A-1B and 2-6, the device does not include a retention frame lumen or a retention frame or wire. Instead, the material of the housing is configured to be elastically deformable between the straightened shape and the retention shape, in the absence of a retention frame or wire. In certain embodiments, the tubular housing is thermally shape set to have a coiled or other retention shape. Thus, in such embodiments, the design and manufacturing of the device is simplified, and the overall size of the device is minimized (or drug payload may be increased if the size of the device remains constant). Advantageously, in embodiments without a retention frame, the tubular housing material serves the functions of (i) forming the drug reservoir lumen, (ii) controlling drug release, and (iii) retaining the device in the bladder upon deployment.

Figure 7A:
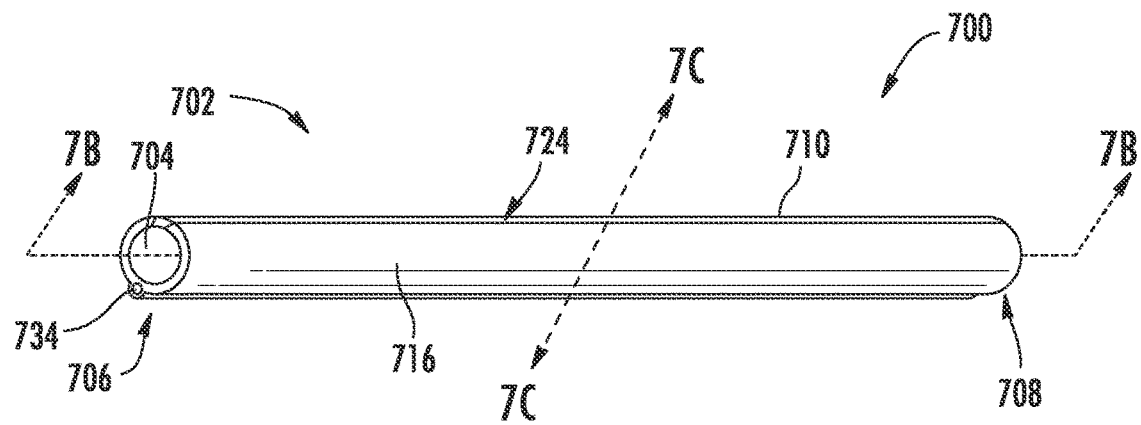
FIG. 7A is a perspective view of another embodiment of a drug delivery device, without drug disposed therein or an elastic retention frame, in a relatively straightened shape, in accordance with the present disclosure.
Figure 7B:
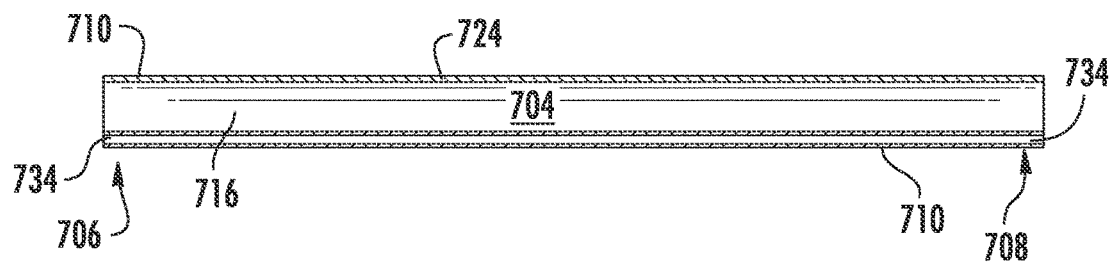
FIG. 7B is a longitudinal cross-sectional view of the drug delivery device shown in FIG. 7A, taken along line 7B-7B.
Figure 7C:
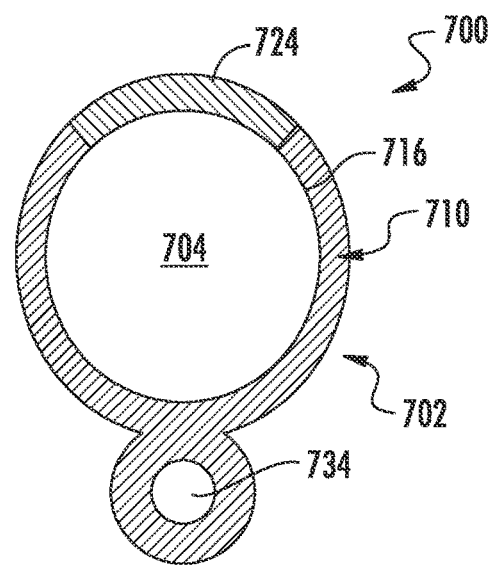
FIG. 7C is a traverse cross-sectional view of the drug delivery device shown in FIG. 7A, taken along line 7C-7C.

In one embodiment, as shown in FIGS. 7A-7C, a drug delivery device 700 is provided that includes an elongated, elastic housing 702 having a drug reservoir lumen 704 extending between a first end 706 and a second end 708. The elastic housing 702 is formed of a tubular wall structure 710 that includes a first wall structure 716 and a second wall structure 724 that are adjacent one another and together form a tube defining the drug reservoir lumen 704, wherein (i) the second wall structure 724, or both the first wall structure 716 and the second wall structure 724, are permeable to water, and (ii) the first wall structure 716 is impermeable to the drug and the second wall structure 724 is permeable to the drug, such that the drug is releasable in vivo by diffusion through the second wall structure 724.

In embodiments in which the first and second wall structures together form a cylindrical tube, any suitable end plugs or closures or thermally formed seals may be used to seal the ends of the tube after the drug is loaded. These end plugs/closures ensure that the drug permeable polymer portions forming a portion of the external tube are the only path for drug release.

In some embodiments, as shown in FIGS. 2 and 3, the wall 206, 205/306, 305 has a substantially constant thickness over its circumference. For example, the inner diameter 210/310 and outer diameter 212/312 of the first and second wall structures 206, 205/306, 305 (which together form the cylindrical tube) are the same.

Figure 4:
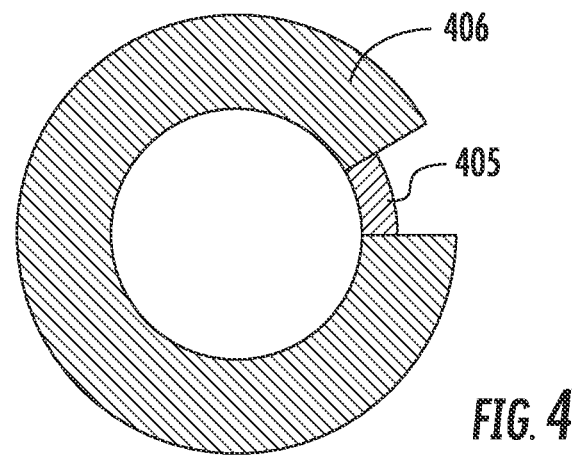
FIG. 4 is a traverse cross-sectional view of one embodiment of a drug delivery device, in accordance with the present disclosure.
Figure 5:
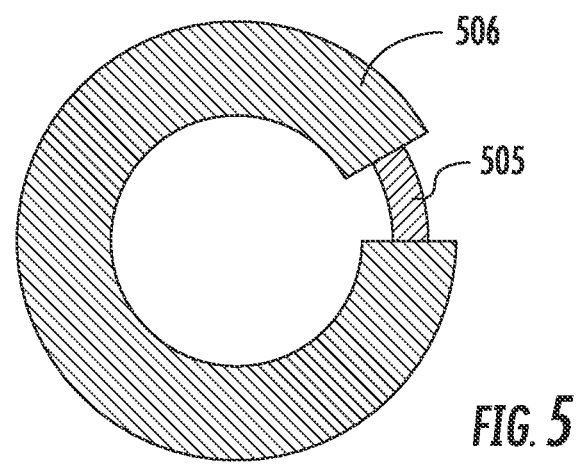
FIG. 5 is a traverse cross-sectional view of one embodiment of a drug delivery device, in accordance with the present disclosure.
Figure 6:
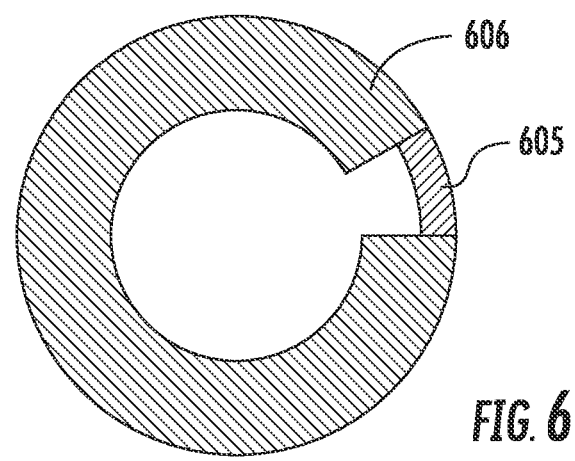
FIG. 6 is a traverse cross-sectional view of one embodiment of a drug delivery device, in accordance with the present disclosure.

In other embodiments, the wall may have a varied thickness over the circumference of the wall, for example as shown in FIGS. 4-6, in which the drug permeable portion (405/505/605) has a thickness that is less than the thickness of the drug impermeable portion (406/506/606). Moreover, the thinner drug permeable wall structure (405/505/605) may be disposed at various positions relative the adjacent, thicker drug impermeable wall structure (406/506/606). As shown in FIG. 4, the thinner drug permeable wall structure 405 may be flush with the inner surface of the drug impermeable wall structure 406 forming the drug reservoir lumen. As shown in FIG. 5, the thinner drug permeable wall 505 may be centered relative the thickness of the drug impermeable wall structure 506. As shown in FIG. 6, the thinner drug permeable wall structure 605 may be flush with the outer surface of the drug impermeable wall structure 606, opposite the surface forming the drug reservoir lumen.

That is, drug release is controlled by drug diffusion through a drug-permeable component defining a portion of the closed device housing. The drug-permeable wall structure may be located, dimensioned, and have material properties to provide the desired rate of controlled drug diffusion from the device.

The particular material and arc angle of the drug permeable portion or wall structure can be selected to achieve a particular drug release profile, i.e., water and drug permeation rates. For example, in certain embodiments, as shown in FIGS. 2 and 3, the second wall structure 205/305 comprises less than 90 percent of a cross sectional area of the tube, in a cross section normal to the longitudinal axis of the tube. In one embodiment, the second wall structure comprises less than 50 percent of a cross sectional area of the tube, in a cross section normal to the longitudinal axis of the tube. In one embodiment, the second wall structure comprises less than 25 percent of a cross sectional area of the tube, in a cross section normal to the longitudinal axis of the tube.

In one embodiment, as shown in FIG. 2, the second wall structure 205 has an arc angle 214 of about 60 degrees of a circumference of the cylindrical tube 200 in the cross-section. In one embodiment, as shown in FIG. 3, the second wall structure 305 has an arc angle 314 of about 30 degrees of a circumference of the cylindrical tube 300 in the cross-section. In one embodiment, the second wall structure has an arc angle of about 10 degrees to about 170 degrees. In one embodiment, the second wall structure has an arc angle of about 15 degrees to about 90 degrees. As used herein, the phrase "about" with reference to the arc angles of the second wall structure refers to the arc angle plus or minus 3 degrees. The second wall structure can be located on the inner curvature (0 degrees), the outer curvature (180 degrees), the top (90 deg), or in-between when the device is formed to have a retention shape as shown in FIG. 1. The top (90 degree) location may be preferable when the second wall structure is formed of a material that significantly swells once absorbing water.

In a second aspect, a drug delivery device having an elongated, elastic housing with a drug reservoir lumen extending between a first closed end and a second closed end has a tubular wall structure that includes a first annular segment formed entirely of a first material which is impermeable to the drug, and a second annular segment formed at least partially of a second material which is permeable to the drug and configured to release the drug in vivo by diffusion through the second material in the second annular segment, where the first annular segment has a first end which is integrally formed and connected with a first end of the second annular segment. Such devices may overcome certain problems associated with conventional extrusion processes. For example, in using certain conventional extrusion processes to make a tubular device body having two wall structures, the portion of the smaller wall structure that includes the drug permeable material (which may be quantified by the arc angle defining the wall when viewed in cross-section normal to the luminal axis) may only be decreased, or narrowed, to a certain extent due to manufacturing limitations. It has been discovered that this wall structure at the narrowest reliably manufacturable arc angle may still yield too large an area for drug diffusion (i.e., drug is released too fast) for certain drugs in a device of a given length. Many other variables or device specifications may be considered for modifying the drug release kinetics in such a situation; however, changing those variables may also undesirably alter mechanical, tolerability, available drug payload volume, or other desired characteristics of the device. It was therefore discovered that an extrusion process may be modified so that the drug permeable material need not extend the full length of the device body. That is, the extrusion process can be modified to implement a discontinuous (or intermittent) feed of the drug permeable material during the process of extruding the drug impermeable wall material of the device body. In this way, the overall dimensions of the tube structure can be maintained, yet advantageously both the length and width of the diffusion portion of the device wall structure can be controlled to give a selected area of, and thus rate for, diffusion of drug for release.

Accordingly, tubular devices have been developed which are designed to reduce or control drug release rates without negatively altering the mechanical properties and suitable dimensions for device deployment and tolerability. In embodiments, the designs reduce drug release rates by reducing the length of the drug permeable regions(s) such that the length runs along only a portion of the overall length of the device. Advantageously, larger arc angles of the drug permeable region(s) can therefore be employed to reduce drug release rates from the device. Additionally, by decreasing the length of the drug permeable region, a lesser amount of drug permeable material, compared to conventional devices, may be used to effect a reduced drug release rate. This is beneficial for the mechanical properties of the device, particularly when the device is used in the bladder.

In one embodiment, as shown in FIGS. 8A-8D, a drug delivery device 800 is provided that includes an elongated, elastic housing 802 having a drug reservoir lumen 804 extending between a first end 806 and a second end 808. The elastic housing 802 is formed of a tubular wall structure 810 that includes a first annular segment 812 and a second annular segment 814. In a preferred embodiment, the first and second annular segments 812, 814 are formed together in an extrusion process.

The first annular segment 812 is formed entirely of a first material 816 which is impermeable to the drug (not shown) disposed in the drug reservoir lumen 804. The first annular segment 812 has a first end 818 which is integrally formed and connected with a first end 820 of the second annular segment 814. The second annular segment 814 is formed of the first material 816 and a second material 824 which is permeable to the drug disposed in the drug reservoir lumen 804, such that the drug is releasable in vivo by diffusion through the second material 824.

In the embodiment illustrated in FIGS. 8A-8D, the second annular segment 814 includes a central portion 826 that extends between an external surface 828 and an internal surface 830 of the tubular wall structure 810. The central portion 826 is formed entirely of the second material 824.

The particular material and arc angle of the second material within the second annular segment can be selected to achieve a particular drug release profile, i.e., water and drug permeation rates, as discussed above with reference to the drug permeable second wall structure within the devices having a drug permeable portion extending along their length (e.g., as shown in FIGS. 7A-7C). For example, in certain embodiments, the portion of the second annular segment comprising the second material comprises less than about 25% of a cross sectional area of the tubular wall structure taken at the central portion. In one embodiment, the portion of the second annular segment comprising the first material forms a first arcuate portion and the portion of the second annular segment comprising the second material forms a second arcuate portion having an arc angle of about 15 degrees to about 120 degrees of a circumference of the tubular wall structure. The first and second arcuate portions are integrally connected and together define the annulus of the second annular segment. In one embodiment, the portion of the second annular segment comprising the second material has an arc angle of about 30 degrees to about 60 degrees.

Once the drug is loaded into the drug reservoir lumen 804, any suitable end plugs or closures or thermally formed seals may be used to seal/close the first and second ends 806, 808 of the elastic housing 802. These end plugs/closures ensure that the second material forming a portion of the elastic housing is the sole path for drug release.

In certain embodiments, as illustrated in FIGS. 8A-8D, the tubular wall structure further includes a third annular segment 832, which is integrally formed and connected with an opposed second end 822 of the second annular segment 814. In one embodiment, the second and third annular segments 814, 832 are formed together in an extrusion process. In one embodiment, the third annular segment 832 is formed entirely of the first material 816.

Figure 8A:
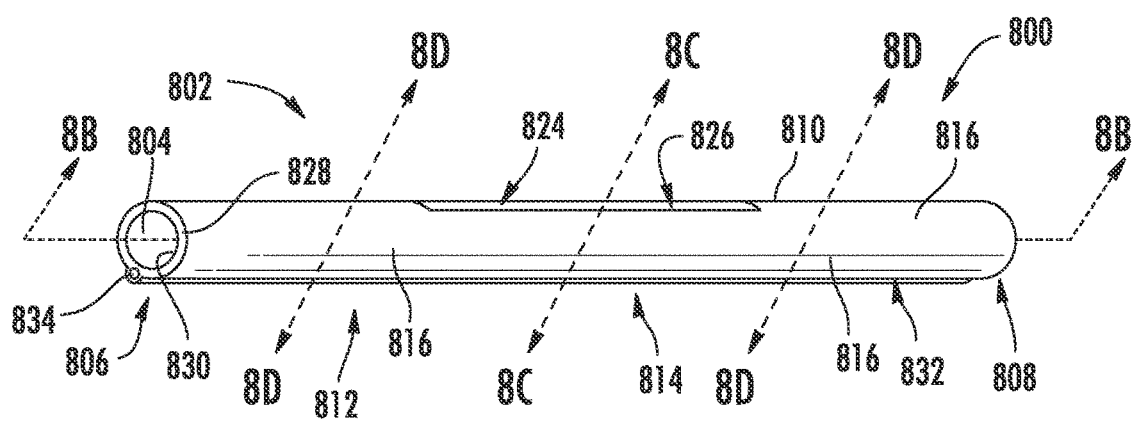
FIG. 8A is a perspective view of another embodiment of a drug delivery device, without drug disposed therein or an elastic retention frame, in a relatively straightened shape, in accordance with the present disclosure.
Figure 8B:
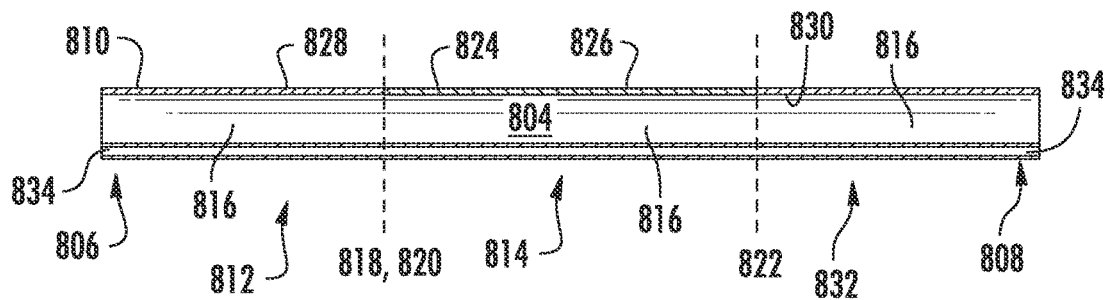
FIG. 8B is a longitudinal cross-sectional view of the drug delivery device shown in FIG. 8A, taken along line 8B-8B.
Figure 8C:
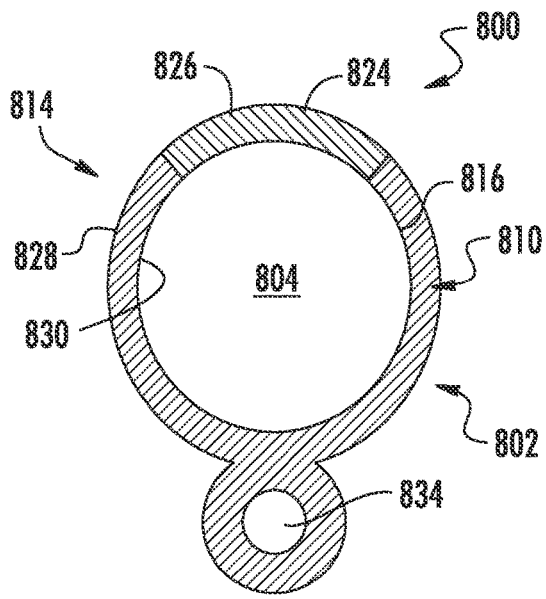
FIG. 8C is a traverse cross-sectional view of the drug delivery device shown in FIG. 8A, taken along line 8C-8C.
Figure 8D:
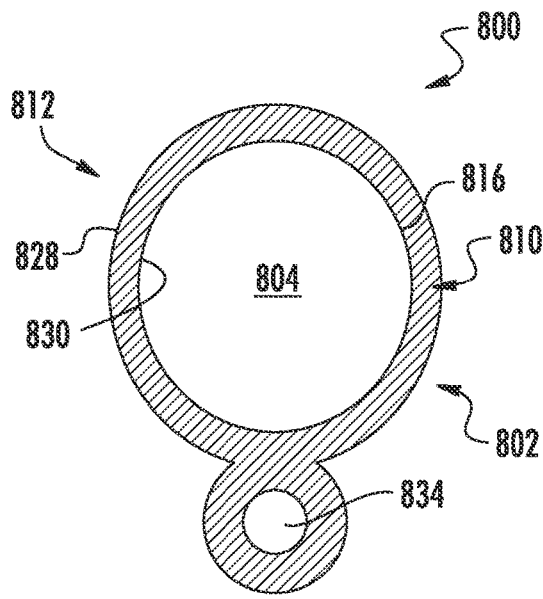
FIG. 8D is a traverse cross-sectional view of the drug delivery device shown in FIG. 8A, taken along lines 8D-8D.
Figure 9A:
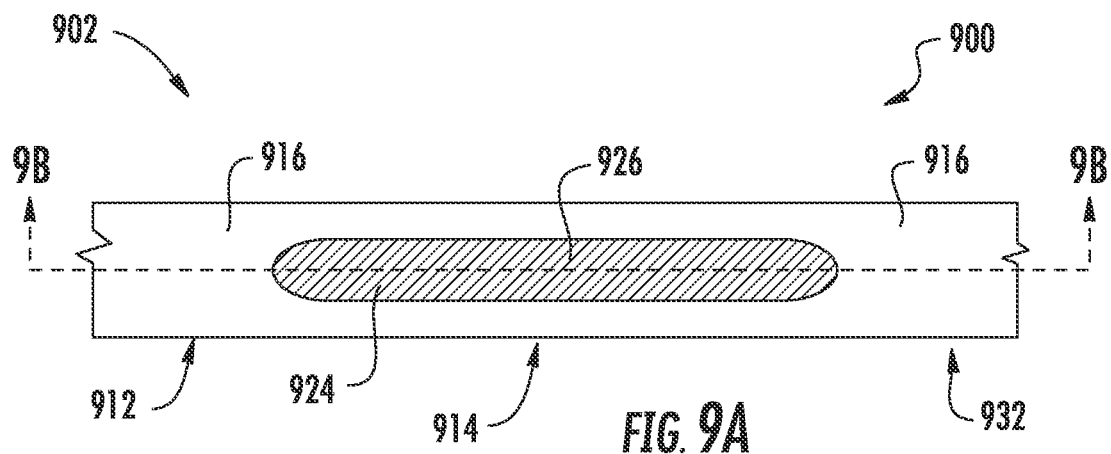
FIG. 9A is partial top plan view of another embodiment of a drug delivery device, without any drug disposed therein, in a relatively straightened shape, in accordance with the present disclosure.
Figure 9B:
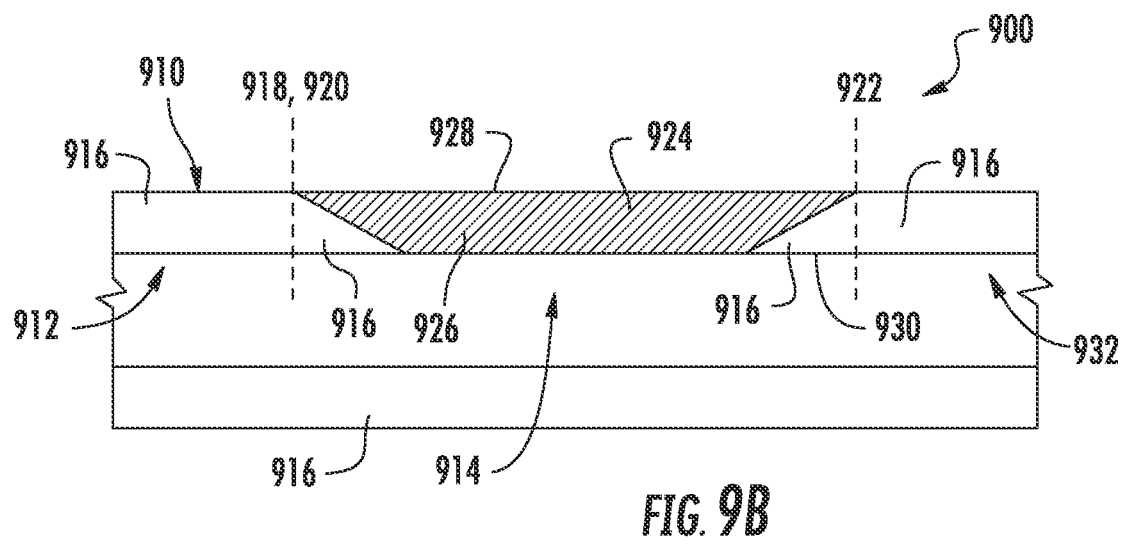
FIG. 9B is a partial longitudinal cross-sectional view of the drug delivery device shown in FIG. 9A, taken along line 9B-9B.

FIGS. 9A-9B illustrate a variation of the drug delivery device 800 shown in in FIGS. 8A-8D, with FIGS. 9A-9B showing only partial longitudinal plan and cross-sectional views of the device 900. The drug delivery device 900 includes an elongated, elastic housing 902 formed of a tubular wall structure. The tubular wall structure includes a first annular segment 912, a second annular segment 914, and a third annular segment 932. The first annular segment is formed of a first material 916, the second annular segment 914 is formed of the first material 916 and a second material 924, and the third annular segment 932 is formed of the first material 916.

In this embodiment, the second annular segment 914 includes a central portion 926 that extends between an external surface 928 and an internal surface 930 of the tubular wall structure 910. The central portion 926 is formed entirely of the second material 924. The second annular segment 914 is shown to include a transition region leading to each of the first and third annular segments 912, 932. In this way, not all of the second material 924 within the second annular segment 914 extends from the external and internal surfaces 928, 930 of the tubular wall structure. The interfaces formed by 918, which is an end of 912, and 920, which is an end of 914, can be angled or straight.

In some embodiments, the tubular wall structure includes one or more additional annular segments that comprise the second material or another material that is permeable to the drug. For example, in one embodiment, the tubular wall structure comprises an additional annular segment, which is integrally formed and connected with an opposed second end of the second annular segment. In one embodiment where the tubular wall structure includes the third annular segment that is connected with an opposed second end of the second annular segment, the tubular wall structure comprises an additional annular segment, which is integrally formed and connected with the opposing freed end of the third annular segment.

In an alternative embodiment, the second material of the device is omitted, such that the absence of the second material defines one or more apertures in the tubular wall structure. Depending on the extrusion process, such an aperture may be substantially round, square, or rectangular, or a slit. Drug release may occur by diffusion through the aperture, or if small enough, drug release from the device may occur by osmotic pressure.

Another embodiment of a drug delivery device is shown in FIGS. 10A-10D. The drug delivery device 1000 includes an elongated, elastic housing 1002 having a drug reservoir lumen 1004 extending between a first end 1006 and a second end 1008. The elastic housing 1002 is formed of a tubular wall structure 1010 that includes a first annular segment 1012 and a second annular segment 1014. In a preferred embodiment, the first and second annular segments 1012, 1014 are formed together in an extrusion process.

The first annular segment 1012 is formed entirely of a first material 1016 which is impermeable to the drug disposed in the drug reservoir lumen 1004. The first annular segment 1012 has a first end 1018 which is integrally formed and connected with a first end 1020 of the second annular segment 1014. The second annular segment 1014 is formed primarily or exclusively of the second material 1024 which is permeable to the drug disposed in the drug reservoir lumen 1004, such that the drug is releasable in vivo by diffusion through the second material 1024. The second annular segment may include a transition region, such that the second annular segment is formed exclusively of the second material in a central part, and formed of a graduated combination of the first and second materials in a transition region at opposed ends about the central part.

Once the drug is loaded into the drug reservoir lumen 1004, any suitable end plugs or closures or thermally formed seals may be used to seal/close the first and second ends 1006, 1008 of the elastic housing 1002. These end plugs/closures ensure that the second material forming a portion of the elastic housing is the only path for drug release.

In certain embodiments, as illustrated in FIGS. 10A-10D, the tubular wall structure 1010 further includes a third annular segment 1032, which is integrally formed and connected with an opposed second end 1022 of the second annular segment 1014. In one embodiment, the second and third annular segments 1014, 1032 are formed together in an extrusion process. In one embodiment, the third annular segment 1032 is formed entirely of the first material 1016.

In a variation of the foregoing illustrated embodiments, an aperture or slit is provided in a drug-impermeable wall structure (e.g., in the first annular segment), in a drug-permeable wall structure (e.g., in the second annular segment), or in at least one end plug closing off the drug reservoir lumen. In such an embodiment, drug release in vivo occurs by both (trans-wall) diffusion and osmosis. The osmotic release contribution through a hole or a slit may not be significant if the drug has a relatively low solubility. However, the hole or slit can serve as a pressure relief vent that can prevent unwanted swelling of the extruded housing.

In embodiments, the length (L) of the second annular segment is less than the total length ($L_T$) of the elastic housing. This beneficially maintains a drug release rate provided by a conventional device or reduces the drug release rate by increasing the arc angle of the second material without increasing the length of the device. In fact, in certain embodiments, the total length of the device can be decreased, while still having a low or reduced drug release rate.

In one embodiment, the length of the second annular segment is from about 5% to about 50% of the length of the elastic body. In another embodiment, the length of the second annular segment is from about 10% to about 30% of the length of the elastic body. In one embodiment, the length ratio of the second annular segment to the elastic body is less than about 0.1. In another embodiment, the length ratio of the second annular segment to the elastic body is less than about 0.4. As used herein, the phrase "about" with reference to lengths refers to the length plus or minus 10 percent of the recited value. In one embodiment, the length of the second annular segment is from about 1 cm to about 8 cm.

Unless otherwise noted, as used herein, the length of a particular element is the longitudinal distance such element extends between its opposing ends. For example, in one embodiment, the length of each annular segment is the longitudinal distance between its first and second opposing ends. For example, in one embodiment, the length of the elastic body is the length between its opposed first and second ends.

In the foregoing embodiments, the first material or the first wall structure, the second material or the first wall structure, or both, is formed of a water permeable material. In a preferred embodiment, the drug is in a solid form (e.g., a tablet or plurality of tablets) and at least a portion of the tubular body is water permeable to permit in vivo solubilization of the drug while in the drug reservoir lumen. In embodiments, the first material or first wall structure may be the only water permeable portion. In other embodiments both the first and second materials/wall structures may be water permeable.

The material(s) for the wall structures and/or annular segments of the present devices can be selected from a variety of suitable materials, for example silicone, polyurethane, ethylene-vinyl acetate (EVA), thermoplastic silicone polyether polyurethane, aliphatic thermoplastic silicone polyether polyurethane, segmented polyether polyurethane, thermoplastic polyether polyurethane, thermoplastic polycarbonate polyurethane, Bionate®PCU, BioSpan® SPU, CarboSil®TSPCU, Elasthane™ TPU, PurSil®TSPU (DSM), other thermoplastic polyurethanes (TPUs), including aliphatic and aromatic, polycarbonate-based thermoplastic polyurethanes, such as Carbothane™ TPU, Tecoflex™ TPU, Tecothane™ TPU, Tecothane™ Soft TPU, Pellethane®TPU, and Tecophilic™ TPU, and combinations or blends thereof.

The second material or wall structure, or other material that is permeable to the drug contained in the drug reservoir, may be a hydrophilic polymer, for example hydrophilic polyurethane, hydrophilic polyesters, and hydrophilic polyamides. In one embodiment, the drug permeable wall structure is Tecophilic™ TPU, HydroThane™ TPU (AdvanSource Biomaterials Corp.), Quadraphilic™ TPU (Biomerics, LLC) (ALC grades are aliphatic polycarbonate-based and ALE grades are aliphatic polyether-based hydrophilic polyurethanes), HydroMed™ (AdvanSource Biomaterials Corp.), or Dryflex® (HEXPOLTPE). Another hydrophilic polymer that may form the drug permeable portion(s) or wall structure(s) is polyether block amide Pebax® MV 1074 SA 01 MED (Arkema), which is a thermoplastic elastomer made of flexible and hydrophilic polyether and rigid polyamide.

In certain embodiments, the first material and/or second material or the first wall structure and/or second wall structure include at least one thermoplastic material. In certain embodiments, the first material or first wall structure, the second material or second wall structure, or both, comprise a polyurethane composition, such as a thermoplastic polyurethane. In certain embodiments, the first wall structure/material comprises a first polyurethane composition and the second wall structure/material comprises a second polyurethane composition, which is different from the first polyurethane composition.

In one embodiment, the first material or first wall structure is formed from Tecoflex™ (e.g., EG-80A), Tecothane™ Soft (e.g., AR-62A), Carbothane™ TPU (e.g., AC-4075A and PC-3575A), or a combination or blend thereof, and the second material or second wall structure is formed from Tecophilic™ TPU (e.g., HP-60D-20, HP-60D-35, HP-60D-60, and HP-93A-100), another hydrophilic TPU, or a combination or blend thereof.

In one embodiment, an inner diameter of the cylindrical tube may be from about 1.0 mm to about 2.5 mm. In one embodiment, an outer diameter of the cylindrical tube is from about 2.0 mm to about 4.1 mm. In one embodiment, a thickness of the first wall structure, the second wall structure, or both, is from about 0.2 mm to about 1.0 mm. In certain embodiments, the thickness of the second wall structure is different than the thickness of the first wall structure.

Thus, as compared to drug delivery systems utilizing a homogenous material (e.g., a blend of permeable and impermeable thermoplastic materials) to form a drug permeable tube, the mechanical properties of a tube utilizing the dual wall structure (e.g., the drug permeable strip embodiments) advantageously can be decoupled from the drug release (e.g., diffusion) properties of the tube. For example, in a single material tube, changing the material of tube inherently affects both the mechanical and diffusion properties of the device. Moreover, the drug release properties of a blended polymer may not be readily predictable. In addition, it is often challenging to achieve a truly homogeneous blend when mixing two thermoplastics. Thus, it requires experimentation to modulate drug release rate with such a tubular drug delivery system.

For use in the bladder, it is important that the device be compliant (i.e., easily flexed, soft feeling) during detrusor muscle contraction in order to avoid or mitigate discomfort and irritation to the patient. Thus, it is noted the durometer of the first and second materials of construction are important, and the proportion of a high durometer material may be limited in constructing a device housing of a given size while keeping it suitably compliant in the bladder. For example, Tecophilic™ thermoplastic polyurethane (Lubrizol Corp.) may have a Shore hardness greater than 70 A, such as from 80 A to 65 D, while other drug impermeable thermoplastic polyurethanes may have a Shore hardness that is less than or greater than Tecophilic™, such as less than 90 A. Accordingly, it can be advantageous to utilize a combination of two different polymeric materials, rather than making the device entirely of the water-swelling hydrophilic, drug-permeable second material, to achieve desired mechanical properties of the tube.

In one embodiment, the first material or first wall structure has a Shore durometer value from about 50 A to about 70 A. In one embodiment, the first material or first wall structure has a Shore durometer value of less than 90 A. In certain embodiments, the second material or second wall structure has a Shore durometer value from about 70 A to about 65 D. The particular material and its thickness and wall area, e.g., arc angle, can be selected to achieve a particular drug release profile, i.e., water and drug permeation rates.

In one embodiment, the first and second materials/wall structures each comprise a thermoplastic polyurethane, the tubular wall structure is elastically deformable from a retention shape suited to retain the device within the bladder to a relatively straightened shape suited for insertion through a lumen into the bladder, and the tubular wall structure is thermally shaped to have the retention shape.

In embodiments where the drug impermeable portion takes up the majority of the tube cross-sectional area and is significantly permeable to water (e.g., Tecoflex EG-80 A) and the tubing has an orifice, the system can be operated to release the drug via both diffusion and osmosis, as long as the reservoir contents (e.g., API and excipients) can create an osmotic pressure gradient across the tubing wall. Thus, the presence of the osmotic orifice can help reduce possible swelling of the reservoir due to osmotic pressure.

In preferred embodiments, the devices described herein are configured to release a therapeutically effective amount of the drug, where the rate of the release of the drug from the drug delivery device is zero order over at least 36 hours. In one embodiment, the rate of the release of the drug from the drug delivery device is essentially zero order over at least 7 days. In embodiments, the device is configured to release a therapeutically effective amount of the drug over a period from 3 days to 90 days, e.g., from 7 days to 30 days, or from 7 days to 14 days. Desirably, the rate of the release of the drug from the drug delivery device is zero order over at least 7 days, e.g., from 7 to 14 days, or longer. In certain embodiments, the device is configured to begin release of the drug after a lag time, for example due to a void space in the inner washer. In certain embodiments, the lag time may at least about 30 minutes, from about 12 hours to about 24 hours, or up to about 2 days.

In preferred embodiments, the drugs are gemcitabine hydrochloride and trospium chloride. In one embodiment, at least 25 mg/day of gemcitabine is released over 7 days. In another embodiment, at least 1 mg/day of trospium chloride is released over 7 days to 3 months. In other embodiments, as discussed in more detail herein, other drugs can be delivered with the devices described herein.

Other Aspects of the Drug Delivery Devices

The devices and methods disclosed herein build upon those described in U.S. Pat. Nos. 8,182,464 and 8,343,516, as well as in U.S. Application Publication No. 2009/0149833 (MIT 12988); U.S. Application Publication No. 2010/0331770 (TB 101); U.S. Application Publication No. 2010/0060309 (TB 108); U.S. Application Publication No. 2011/0202036 (TB 107); U.S. Application Publication No. 2011/0152839 (TB 112); PCT/US11/46843, filed Aug. 5, 2011 (TB 113); U.S. application Ser. No. 13/267,560, filed Oct. 6, 2011 (TB 116); and U.S. application Ser. No. 13/267,469, filed Oct. 6, 2011 (TB 117), each of which is incorporated herein by reference.

In certain embodiments, the devices are configured for intravesical insertion and retention in a patient. For example, the devices can be elastically deformable between a relatively straightened shape suited for insertion through a lumen into a body cavity of a patient and a retention shape suited to retain the device within the body cavity, such as shown in FIG. 1A. When in the retention shape after deployment in the bladder, for example, the devices may resist excretion in response to the forces of urination or other forces. Since the devices are designed to be retained within a lumen or body cavity, they are capable of overcoming some of the deficiencies of conventional treatments, such as those related to the bladder. The devices described herein can be inserted once and release drug over a desired period of time without surgery or frequent interventions. The devices, as a result, may reduce the opportunity for infection and side effects, increase the amount of drug delivered locally or regionally to the bladder, or improve the quality of life of the patient during the treatment process. After drug release, the devices can be removed, for example by cystoscope and forceps, or be bioerodible, at least in part, to avoid a retrieval procedure.

The device may be loaded with at least one drug in the form of one or more solid drug units, such as tablets, capsules, or pellets. Providing one or more drugs in solid form to a patient is often advantageous. Solid drugs can provide a relatively large drug payload volume to total device volume and potentially enhance stability of the drugs during shipping, storage, before use, or before drug release. Solid drugs, however, should be solubilizable in vivo in order to diffuse into through the drug-permeable component and into the patient's surrounding tissues in a therapeutically effective amount.

The drug reservoir lumen may hold one or several drug tablets or other solid drug units. In one embodiment, the device holds from about 10 to 100 cylindrical drug tablets, such as mini-tablets, among a number of discrete drug reservoir lumens. In certain embodiments, the mini-tablets may each have a diameter of about 1.0 to about 3.3 mm, such as about 1.5 to about 3.1 mm, and a length of about 1.5 to about 4.7 mm, such as about 2.0 to about 4.5 mm.

The devices may be inserted into a patient using a cystoscope or catheter. Typically, a cystoscope for an adult human has an outer diameter of about 5 mm and a working channel having an inner diameter of about 2.4 mm to about 2.6 mm. In embodiments, a cystoscope may have a working channel with a larger inner diameter, such as an inner diameter of 4 mm or more. Thus, the device may be relatively small in size. For example, when the device is elastically deformed to the relatively straightened shape, the device for an adult patient may have a total outer diameter that is less than about 2.6 mm, such as between about 2.0 mm and about 2.4 mm. For pediatric patients, the dimensions of the device are anticipated to be smaller, e.g., proportional for example based on the anatomical size differences and/or on the drug dosage differences between the adult and pediatric patients. In addition to permitting insertion, the relatively small size of the device may also reduce patient discomfort and trauma to the bladder.

In one embodiment, the overall configuration of the device promotes in vivo tolerability for most patients. In a particular embodiment, the device is configured for tolerability based on bladder characteristics and design considerations described in U.S. Application Publication No. 2011/0152839 (TB 112), which is incorporated herein by reference.

Within the three-dimensional space occupied by the device in the retention shape, the maximum dimension of the device in any direction preferably is less than 10 cm, the approximate diameter of the bladder when filled. In some embodiments, the maximum dimension of the device in any direction may be less than about 9 cm, such as about 8 cm, 7 cm, 6 cm, 5 cm, 4.5 cm, 4 cm, 3.5 cm, 3 cm, 2.5 or smaller. In particular embodiments, the maximum dimension of the device in any direction is less than about 7 cm, such as about 6 cm, 5 cm, 4.5 cm, 4 cm, 3.5 cm, 3 cm, 2.5 cm or smaller. In preferred embodiments, the maximum dimension of the device in any direction is less than about 6 cm, such as about 5 cm, 4.5 cm, 4 cm, 3.5 cm, 3 cm, 2.5 cm or smaller. More particularly, the three-dimension space occupied by the device is defined by three perpendicular directions. Along one of these directions the device has its maximum dimension, and along the two other directions the device may have smaller dimensions. For example, the smaller dimensions in the two other directions may be less than about 4 cm, such as about 3.5 cm, 3 cm, 2.5 cm or less. In a preferred embodiment, the device has a dimension in at least one of these directions that is less than 3 cm.

In some embodiments, the device may have a different dimension in at least two of the three directions, and in some cases in each of the three directions, so that the device is non-uniform in shape. Due to the non-uniform shape, the device may be able to achieve an orientation of reduced compression in the empty bladder, which also is non-uniform in shape. In other words, a particular orientation of the device in the empty bladder may allow the device to exert less contact pressure against the bladder wall, making the device more tolerable for the patient.

The overall shape of the device may enable the device to reorient itself within the bladder to reduce its engagement or contact with the bladder wall. For example, the overall exterior shape of the device may be curved, and all or a majority of the exterior or exposed surfaces of the device may be substantially rounded. The device also may be substantially devoid of sharp edges, and is exterior surfaces may be formed from a material that experiences reduced frictional engagement with the bladder wall. Such a configuration may enable the device to reposition itself within the empty bladder so that the device applies lower contact pressures to the bladder wall. In other words, the device may slip or roll against the bladder wall into a lower energy position, meaning a position in which the device experiences less compression.

In one embodiment, the device is generally planar in shape even though the device occupies three-dimensional space. Such a device may define a minor axis, about which the device is substantially symmetrical, and a major axis that is substantially perpendicular to the minor axis. The device may have a maximum dimension in the direction of the major axis that does not exceed about 6 cm, and in particular embodiments is less than 5 cm, such as about 4.5 cm, about 4 cm, about 3.5 cm, about 3 cm, or smaller. The device may have a maximum dimension in the direction of the minor axis that does not exceed about 4.5 cm, and in particular embodiments is less than 4 cm, such as about 3.5 cm, about 3 cm, or smaller. The device is curved about substantially its entire exterior perimeter in both a major cross-sectional plane and a minor cross-sectional plane. In other words, the overall exterior shape of the device is curved and the cross-sectional shape of the device is rounded. Thus, the device is substantially devoid of edges, except for edges on the two flat ends, which are completely protected within the interior of the device when the device lies in a plane. These characteristics enable the device to reorient itself into a position of reduced compression when in the empty bladder.

The device also may be small enough in the retention shape to permit intravesical mobility. In particular, the device when deployed may be small enough to move within the bladder, such as to move freely or unimpeded throughout the entire bladder under most conditions of bladder fullness, facilitating patient tolerance of the device. Free movement of the device also facilitates uniform drug delivery throughout the entire bladder.

The device also may be configured to facilitate buoyancy, such as with the use of low density materials of construction for the housing components and/or by incorporating gas or gas generating materials into the housing, as described for example in U.S. Application Publication No. 2012/0089121 (TB 116), which is incorporated herein by reference. In general, the device in the dry and drug-loaded state may have a density in the range of about 0.5 g/mL to about 1.5 g/mL, such as between about 0.7 g/mL to about 1.3 g/mL. In some embodiments, the device in the dry and drug-loaded state has a density that is less than 1 g/mL.

The implantable drug delivery device can be made to be completely or partially bioerodible so that no explanation, or retrieval, of the device is required following release of the drug formulation. In some embodiments, the device is partially bioerodible so that the device, upon partial erosion, breaks into non-erodible pieces small enough to be excreted from the bladder. As used herein, the term "bioerodible" means that the device, or part thereof, degrades in vivo by dissolution, enzymatic hydrolysis, erosion, resorption, or combinations thereof. In one embodiment, this degradation occurs at a time that does not interfere with the intended kinetics of release of the drug from the device. For example, substantial erosion of the device may not occur until after the drug formulation is substantially or completely released. In another embodiment, the device is erodible and the release of the drug formulation is controlled at least in part by the degradation or erosion characteristics of the erodible device body. The devices described herein may be designed to conform with the characteristics of those described in U.S. Application Publication No. 2012/0089122 (TB 117), which is incorporated herein by reference.

The drug delivery device may be sterilized before being inserted into a patient. In one embodiment, the device is sterilized using a suitable process such as gamma irradiation or ethylene oxide sterilization, although other sterilization processes may be used.

Retention of the Device in a Body Cavity

The devices described herein are elastically deformable between a relatively straightened or uncoiled shape suited for insertion through a lumen into the bladder (or other body cavity) of a patient and a retention or coiled shape suited to retain the device within the urinary bladder (or other body cavity). In certain embodiments, the drug delivery device may naturally assume the retention shape and may be deformed, either manually or with the aid of an external apparatus, into the relatively straightened shape for insertion into the body. Once deployed the device may spontaneously or naturally return to the initial, retention shape for retention in the body.

Figure 10A:
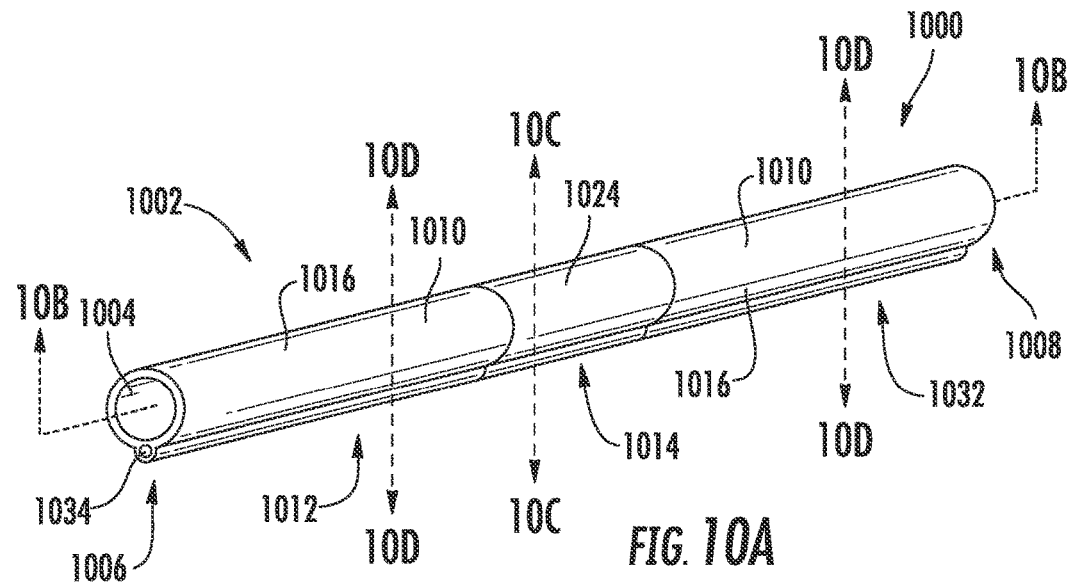
FIG. 10A is a perspective view of another embodiment of a drug delivery device, in accordance with the present disclosure.
Figure 10B:
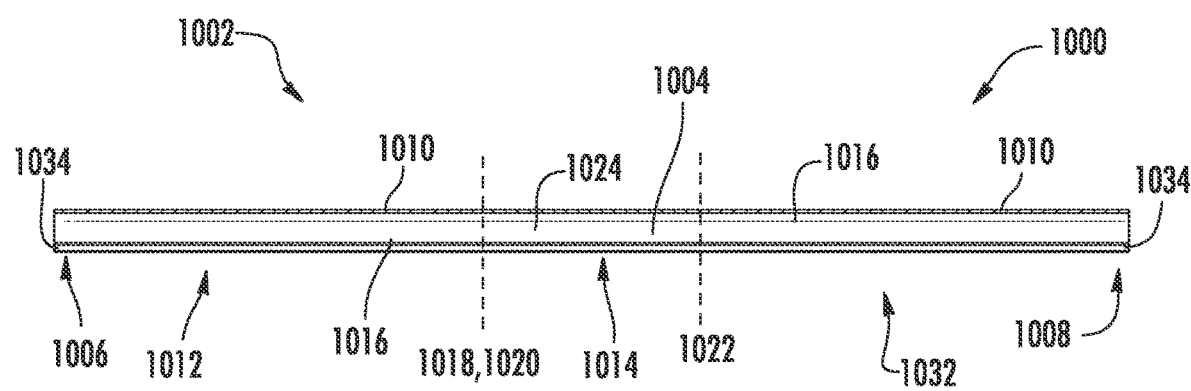
FIG. 10B is a longitudinal cross-sectional view of the drug delivery device shown in FIG. 10A, taken along line 10B-10B.
Figure 10C:
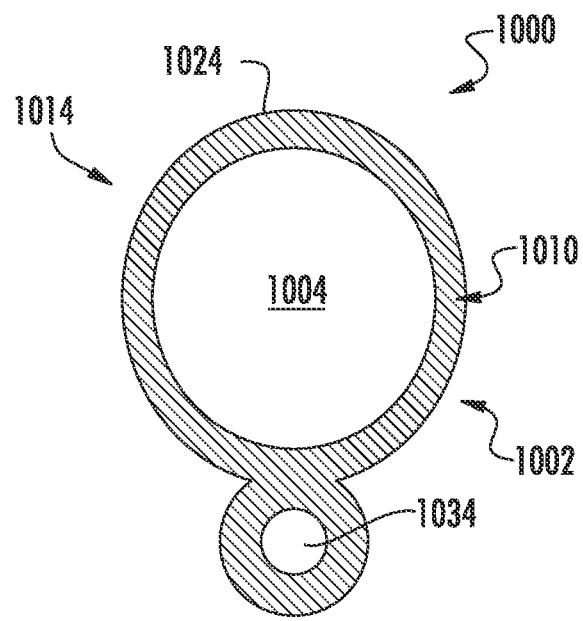
FIG. 10C is a traverse cross-sectional view of the drug delivery device shown in FIG. 10A, taken along line 10C-10C.
Figure 10D:
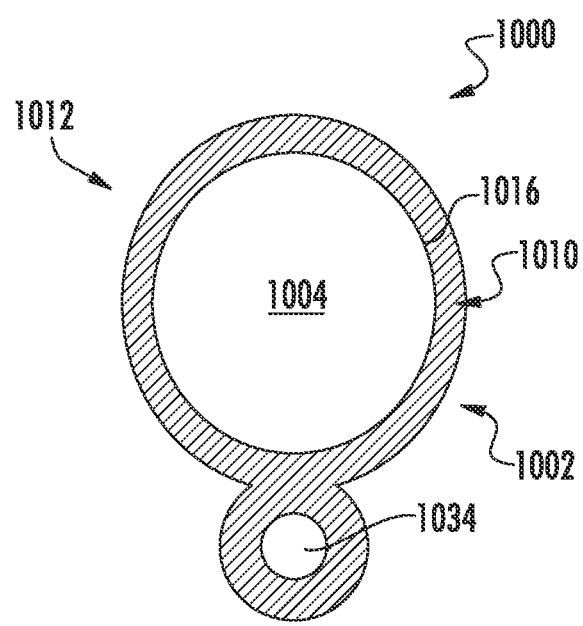
FIG. 10D is a traverse cross-sectional view of the drug delivery device shown in FIG. 10A, taken along lines 10D-10D.

For the purposes of this disclosure, the term "retention shape" generally denotes any shape suited for retaining the device in the intended implantation location, including, but not limited to, a coiled or "pretzel" shape, such as shown in FIG. 1A, which is suited for retaining the device in the bladder. Similarly, the term "relatively straightened shape" generally denotes any shape suited for deploying the drug delivery device into the body, including, but not limited to, a linear or elongated shape, such as shown in FIGS. 7A, 8A, 10A, which is suited for deploying the device through the working channel of catheter, cystoscope, or other deployment instrument positioned in a lumen of the body, such as the urethra.

In some embodiments, as shown in FIGS. 7A-7C, 8A-8D, and 10A-10D, the device further includes retention frame lumen 734, 834, 1034 and a retention frame (not shown) positioned in the retention frame lumen. For example, the retention frame lumen and retention frame may be as described in U.S. Application Publication No. 2010/0331770 (TB 101); U.S. Application Publication No. 2010/0060309 (TB 108); U.S. Application Publication No. 2011/0202036 (TB 107); and U.S. Application Publication No. 2011/0152839 (TB 112).

In other embodiments, as shown in FIGS. 1A-1B and 2-6, the device does not include a retention frame lumen or a retention frame or wire. Instead, the material of the housing is configured to be elastically deformable between the straightened shape and the retention shape, in the absence of a retention frame or wire. In such embodiments, the design and manufacturing of the device is simplified, and the overall size of the device is minimized (or drug payload may be increased where the size of the device remains constant). Advantageously, in embodiments without a retention frame, the tubular housing material serves the functions of (i)

forming the drug reservoir lumen, (ii) controlling drug release, and (iii) retaining the device in the bladder upon deployment.

For example, the tubular housing may be thermally shape set to have the retention shape. Thus, the housing may comprise one or more thermoplastic materials that are suitable to be thermally formed into the retention shape. In certain embodiments, a drug delivery device includes a tubular housing having a closed drug reservoir lumen bounded by a wall structure comprising at least one thermoplastic material, wherein (i) at least a portion of the wall structure is water permeable and at least a portion of the wall structure is drug permeable, (ii) the tubular housing is elastically deformable from a retention shape suited to retain the device within the bladder to a relatively straightened shape suited for insertion through a lumen into the bladder, and (iii) the tubular wall is thermally shaped to have the retention shape.

In certain embodiments where the wall structure comprises first and second wall structures or first and second annular segments, the first and second wall structures/segments are each a thermoplastic polyurethane and the tubular housing is thermally shaped to have the retention shape. In one embodiment, the tubular wall has a spring constant effective to impede the device from assuming the relatively straightened shape once implanted in the bladder. Thus, the properties of the tubular wall may cause the device to function as a spring, deforming in response to a compressive load but spontaneously returning to its initial shape once the load is removed.

In certain embodiments, the devices may naturally assume the retention shape, may be deformed into the relatively straightened shape, and may spontaneously return to the retention shape upon insertion into the body. The tubular wall structure in the retention shape may be shaped for retention in a body cavity, and in the relatively straightened shape may be shaped for insertion into the body through the working channel of a deployment instrument such as a catheter or cystoscope. To achieve such a result, the tubular wall structure may have an elastic limit, modulus, and/or spring constant selected to impede the device from assuming the relatively lower-profile shape once implanted. Such a configuration may limit or prevent accidental expulsion of the device from the body under expected forces. For example, the device may be retained in the bladder during urination or contraction of the detrusor muscle.

In a preferred embodiment, the device is elastically deformable between a relatively straightened shape suited for insertion through a catheter or cystoscope extending through a patient's urethra of a patient and a curved or coiled shape suited to retain the device within the bladder (i.e., to prevent its expulsion from the bladder during urination) following release of the device from the end of the catheter or cystoscope.

As shown in FIG. 1A, the retention shape may include a coiled or "pretzel" shape. The pretzel shape essentially comprises at least two sub-circles, each having its own smaller arch and sharing a common larger arch. When the pretzel shape is first compressed, the larger arch absorbs the majority of the compressive force and begins deforming, but with continued compression the smaller arches overlap, and subsequently, all three of the arches resist the compressive force. The resistance to compression of the device as a whole increases once the two sub-circles overlap, impeding collapse and voiding of the device as the bladder contracts during urination.

The wall structure in the retention shape may have a two-dimensional structure that is confined to a plane, a three-dimensional structure, such as a structure that occupies the interior of a spheroid, or some combination thereof. The retention shape may comprise one or more loops, curls, or sub-circles, connected either linearly or radially, turning in the same or in alternating directions, and overlapping or not overlapping. The retention shape may comprise one or more circles or ovals arranged in a two-dimensional or a three-dimensional configuration, the circles or ovals may be either closed or opened, having the same or different sizes, overlapping or not overlapping, and joined together at one or more connecting points. The retention shape also may be a three-dimensional structure that is shaped to occupy or wind about a spheroid-shaped space, such as a spherical space, a space having a prorate spheroid shape, or a space having an oblate spheroid shape. The wall structure in the retention shape may be shaped to occupy or wind about a spherical space. The wall structure in the retention shape may generally take the shape of two intersecting circles lying in different planes, two intersecting circles lying in different planes with inwardly curled ends, three intersecting circles lying in different planes, or a spherical spiral. In each of these examples, the wall structure can be stretched to the linear shape for deployment through a deployment instrument. The wall structure may wind about or through the spherical space, or other spheroid-shaped space, in a variety of other manners. Examples of alternative configurations are described in the U.S. patent applications incorporated by reference herein.

Advantageously, drug delivery devices utilizing thermally formed coextruded tubing with drug permeable and drug impermeable portions integrate three functional components (drug reservoir/housing, drug permeation route, and retentive feature) into a single thermally shaped co-extruded tubing component, which simplifies the device design and the ability to control the drug release rate. As discussed herein, in such devices, the drug release rate can be relatively easily modified by controlling the angle and thickness of the drug permeable portion (e.g., strip) without changing whole tube housing material.

A thermally shaped coextruded tubular housing may be loaded with drug tablets and both ends may be sealed thermally or with adhesive (such as Tecoflex 1-MP TPU Adhesive, Lubrizol). If the local tube cross-section deformation or tube kinking occurs, the tablet loading will be difficult. Therefore, the tube dimensions should be chosen to prevent kinking when the tube is thermally shaped. The critical bending radius of curvature (R*) of elastic tubes under pure bending condition can be approximated using the following equation:

$$R^* \approx \frac{3}{\sqrt{2}} \frac{r^2 \sqrt{1-v^2}}{w}$$

where v is Poisson's ratio, r is the mean radius (i.e. (ID+OD)/4), and w is the tube wall thickness (Guarracino, F. 2003. *On the analysis of cylindrical tubes under flexure: theoretical formulation, experimental data and finite element analyses. Thin Wall Struct;* 41:127-147). As an illustration, FIG. 6 is a multi-coiled polyurethane tube with 2.16 mm inner diameter and 0.81 mm wall thickness. With a Poisson's ratio v of 0.49 for polyurethanes (H. J. Qia, M. C. Boyce, *Stress-strain behavior of thermoplastic polyurethanes,* 2005 *Mechanics of Materials;* 37(8):817-839), the estimated critical radius is 0.5 cm. Therefore, when thermally shaping a polyurethane tube, the radius of curvature should be above 0.5 cm all along the length of the tube to prevent kinking. Thus, in one embodiment, the retention shape comprises at least one loop having a radius of curvature of at least 0.5 cm.

The Drug Formulation and Solid Drug Tablets

The drug reservoir lumen may contain a drug in various forms, including solids, semi-solids, liquids, suspensions, gels, etc. In a preferred embodiment, as shown in FIGS. 1A and 1B, a drug formulation is formed into solid drug units 108 that are loaded into the drug reservoir lumen 106 of the device 100. Each of the solid drug units is a solid, discrete object that substantially retains a selectively imparted shape (at the temperature and pressure conditions to which the delivery device normally will be exposed during assembly, storage, and handling before implantation). The drug units may be in the form of tablets, capsules, pellets, or beads, although other configurations are possible.

The solid drug units can be formed using a stable and scalable manufacturing process. Particularly, the drug tablets are sized and shaped for loading into and efficiently storing the tablets in a housing of a drug delivery device that can be deployed into the bladder or another cavity, lumen, or tissue site in a patient in a minimally invasive manner.

The solid drug units may be made by a direct powder compaction or tableting process, a molding process, or other processes known in the pharmaceutical arts. Suitable drug tablet forming methods are described in U.S. Application Publication No. 2010/0330149 (TB 102), which is incorporated herein by reference. The drug formulation also may be loaded into the device housing in workable form and may cure therein. For example, in embodiments in which the drug formulation is configured to be melted and solidified, the drug formulation can be melted, injected into the device housing in melted form and then solidified. The drug formulation also may be extruded with the device housing, may cure within the housing, and subsequently may be cut in spaced positions along the length of the housing to form segments with exposed surface areas of drug.

The solid drug unit includes a drug formulation, which includes a drug content and may include an excipient content. In a preferred embodiment, the drug content includes one or more drugs, or active pharmaceutical ingredients (API), while the excipient content includes one or more pharmaceutically acceptable excipients. The drug formulation can include essentially any therapeutic, prophylactic, or diagnostic agent, such as one that would be useful to deliver locally to a body cavity or lumen or regionally about the body cavity or lumen. The drug formulation may consist only of the API, or one or more excipients may be included.

As used herein, the term "drug" with reference to any specific drug described herein includes its alternative forms, such as salt forms, free acid forms, free base forms, and hydrates. The term "excipient" is known in the art, and representative examples of excipients useful in the present drug units may include ingredients such as binders, lubricants, glidants, disintegrants, colors, fillers, diluents, coatings, or preservatives, as well as other non-active ingredients to facilitate manufacturing, stability, dispersibility, wettability, and/or release kinetics of the drug or administering the drug unit. The drug may be small molecule, macromolecule, biologic, or metabolite, among other forms/types of active ingredients.

In order to maximize the amount of drug that can be stored in and released from a given drug delivery device of a selected (small) size, the drug unit preferably comprises a high weight fraction of drug or API, with a reduced or low weight fraction of excipients as are required for solid drug unit manufacturing and device assembly and use considerations. For the purposes of this disclosure, terms such as "weight fraction," "weight percentage," and "percentage by weight" with reference to drug, or API, refers to the drug or API in the form employed, such as in salt form, free acid form, free base form, or hydrate form. For example, a solid drug unit that has 90% by weight of a drug in salt form may include less than 90% by weight of that drug in free base form.

In one embodiment, the solid drug unit is more than 50% by weight drug. In another embodiment, 75% or more of the weight of the solid drug unit is drug, with the remainder of the weight comprising excipients, such as lubricants and binders that facilitate making the solid drug unit. For the purposes of this disclosure, the term "high weight fraction" with reference to the drug or API means that excipients constitute less than 25 wt %, preferably less than 20 wt %, more preferably less than 15 wt %, and even more preferably less than 10 wt % of the solid drug unit. In some cases, the drug content comprises about 75% or more of the weight of the solid drug unit. More particularly, the drug content may comprise about 80% or more of the weight of the drug tablet. For example, the drug content may comprise between about 85% and about 99.9% of the weight of the solid drug unit. In some embodiments, the excipient content can be omitted completely.

In one embodiment, the drug and excipients are selected and the solid drug unit formulated to be water soluble, so that the solid drug units can be solubilized when the device is located within the bladder, to release the solubilized drug.

The individual solid drug units may have essentially any selected shape and dimension that fits within the devices described herein. In one embodiment, the solid drug units are sized and shaped such that the drug reservoir lumens in the housings are substantially filled by a select number of solid drug units. Each solid drug unit may have a cross-sectional shape that substantially corresponds to a cross-sectional shape of the drug reservoir lumen of a particular housing. For example, the drug units may be substantially cylindrical in shape for positioning in a substantially cylindrical drug reservoir lumen. Once loaded, the solid drug units can, in some embodiments, substantially fill the drug reservoir lumens, forming the drug housing portion.

In one embodiment, the solid drug units are shaped to align in a row when the device is in its deployment configuration. For example, each solid drug unit may have a cross-sectional shape that corresponds to the cross-sectional shape of the drug reservoir lumens in the housing, and each solid drug unit may have end face shapes that correspond to the end faces of adjacent solid drug units. The interstices or breaks between solid drug units can accommodate deformation or movement of the device, such as during deployment, while permitting the individual drug units to retain their solid form. Thus, the drug delivery device may be relatively flexible or deformable despite being loaded with a solid drug, as each drug unit may be permitted to move with reference to adjacent drug units.

In embodiments in which the solid drug units are designed for insertion or implantation in a lumen or cavity in the body, such as the bladder, via a drug delivery device, the drug units may be "mini-tablets" that are suitably sized and shaped for insertion through a natural lumen of the body, such as the urethra. For the purpose of this disclosure, the term "mini-tablet" generally indicates a solid drug unit that is substantially cylindrical in shape, having end faces and a side face that is substantially cylindrical. The mini-tablet has a diameter, extending along the end face, in the range of about 1.0 to about 3.2 mm, such as between about 1.5 and about 3.1 mm. The mini-tablet has a length, extending along the side face, in the range of about 1.7 mm to about 4.8 mm, such as between about 2.0 mm and about 4.5 mm. The friability of the tablet may be less than about 2%. Embodiments of solid drug units and systems and methods of making the same are further described below with reference to U.S. patents and patent Applications incorporated by reference herein.

In one embodiment, the drug formulation is in a solid form. In another embodiment, the drug formulation is in semi-solid form, such as an emulsion or suspension; a gel or a paste. For example, the drug formulation may be a highly viscous emulsion or suspension. As used herein, the solid form includes semi-solid forms unless otherwise indicated. In one embodiment, the drug formulation is in a liquid form.

The drug may be a low solubility drug. As used herein, the term "low solubility" refers to a drug having a solubility from about 0.01 mg/mL to about 10 mg/mL water at 37° C. In other embodiments, the drug is a high solubility drug. As used herein, the term "high solubility" refers to a drug having a solubility above about 10 mg/mL water at 37° C. For example, the approximate solubilities of certain drug formulations are: trospium chloride: 500 mg/mL; lidocaine HCl: 680 mg/mL; lidocaine base: 8 mg/mL, gemcitabine HCl: 80 mg/mL; gemcitabine base: 15 mg/mL; oxybutynin HCl: 50 mg/mL; oxybutynin base: 0.012 mg/mL; and tolterodine tartrate: 12 mg/mL.

In one embodiment, the drug delivery device is used to treat renal or urinary tract cancer, such as bladder cancer and prostate cancer. Drugs that may be used include antiproliferative agents, cytotoxic agents, chemotherapeutic agents, or combinations thereof. Representative examples of drugs which may be suitable for the treatment of urinary tract cancer include Bacillus Calmette Guerin (BCG) vaccine, docetaxel, cisplatin, doxorubicin, valrubicin, gemcitabine, mycobacterial cell wall-DNA complex (MCC), methotrexate, vinblastine, thiotepa, mitomycin (e.g., mitomycin C), fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may comprise a monoclonal antibody, a TNF inhibitor, an antileukin, or the like. The drug also may be an immunomodulator, such as a TLR agonist, including imiquimod or another TLR7 agonist. The drug also may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. Other examples include celecoxib, erolotinib, gefitinib, paclitaxel, polyphenon E, valrubicin, neocarzinostatin, apaziquone, Belinostat, Ingenol mebutate, Urocidin (MCC), Proxinium (VB 4845), BC 819 (BioCancell Therapeutics), Keyhole limpet haemocyanin, LOR 2040 (Lorus Therapeutics), urocanic acid, OGX 427 (OncoGenex), and SCH 721015 (Schering-Plough). The drug treatment may be coupled with a conventional radiation or surgical therapy targeted to the cancerous tissue.

In one embodiment, the devices described herein are loaded with an anesthetic agent, analgesic agent, and combinations thereof. The anesthetic agent may be an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocaine, ropivacaine, and trimecaine. Representative examples of aminoesters or ester-class anesthetics include amylocaine, benzocaine, butacaine, chloroprocaine, cocaine, cyclomethycaine, dimethocaine, hexylcaine, larocaine, meprylcaine, metabutoxycaine, orthocaine, piperocaine, procaine, proparacaine, propoxycaine, proxymetacaine, risocaine, and tetracaine. These anesthetics typically are weak bases and may be formulated as a salt, such as a hydrochloride salt, to render them water-soluble, although the anesthetics also can be used in free base or hydrate form. Other anesthetics, such as lontocaine, also may be used. The drug also can be an antimuscarinic compound that exhibits an anesthetic effect, such as oxybutynin or propiverine. The drug also may include other drugs described herein, alone or in combination with a local anesthetic agent.

In certain embodiments, the analgesic agent includes an opioid. Representative examples of opioid agonists include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated.

Representative examples of other suitable pain relieving agents include such agents as salicyl alcohol, phenazopyridine hydrochloride, acetaminophen, acetylsalicylic acid, flufenisal, ibuprofen, indoprofen, indomethacin, and naproxen.

In certain embodiments, the drug delivery device is used to treat inflammatory conditions such as interstitial cystitis (IC), radiation cystitis, painful bladder syndrome, prostatitis, urethritis, post-surgical pain, and kidney stones. Non-limiting examples of specific drugs for these conditions include lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, cyclosporine, or combinations thereof. For kidney stones, the drug(s) may be selected to treat pain and/or to promote dissolution of renal stones.

Other non-limiting examples of drugs that may be used in the treatment of IC include nerve growth factor monoclonal antibody (MAB) antagonists, such as Tanezumab, and calcium channel alpha-2-delta modulators, such as PD-299685 or gabepentin. Evidence suggests that the bladder expresses nerve growth factor (NGF) locally, since exogenously delivered NGF into the bladder induces bladder hyperactivity and increases the excitability of dissociated bladder afferent neurons (Nature Rev Neurosci 2008; 9:453-66). Accordingly, it would be advantageous to locally deliver a MAB or other agent against NGF using the described delivery devices, significantly reducing the total dose needed for therapeutic efficacy. Evidence also suggests that binding of the alpha-2-delta unit of voltage-sensitive calcium channels, such as with gabapentin, may be effective in the treatment of diseases of neuropathic pain such as fibromyalgia and that there may be common mechanisms between IC and diseases of neuropathic pain (See Tech Urol. 2001 March, 7(1):47-49). Accordingly, it would be advantageous to locally deliver a calcium channel alpha-2-delta modulator, such as PD-299685 or gabepentin, using the described delivery devices, minimizing does-related systemic toxicities in the treatment of IC.

Other intravesical cancer treatments include small molecules, such as Apaziquone, adriamycin, AD-32, doxorubicin, doxetaxel, epirubicin, gemcitabine, HTI-286 (hemiasterlin analogue), idarubicin, γ-linolenic acid, mitozantrone, meglumine, and thiotepa; large molecules, such as EGF-dextran, HPC-doxorubicin, IL-12, IFN-α2b, IFN-γ, α-lactalbumin, p53 adenovector, TNFα; combinations, such as Epirubicin+BCG, IFN+farmarubicin, Doxorubicin+5-FU (oral), BCG+IFN, and Pertussis toxin+cystectomy; activated cells, such as macrophages and T cells; intravesical infusions such as IL-2 and Doxorubicin; chemosensitizers, such as BCG+antifirinolytics (paramethylbenzoic acid or aminocaproic acid) and Doxorubicin+verapimil; diagnostic/imaging agents, such as Hexylaminolevulinate, 5-aminolevulinic acid, Iododexyuridine, HMFG1 Mab+Tc99m; and agents for the management of local toxicity, such as Formaline (hemorrhagic cystitis).

The drug delivery device can be used, for example, to treat urinary incontinence, frequency, or urgency, including urge incontinence and neurogenic incontinence, as well as trigonitis. Drugs that may be used include anticholinergic agents, antispasmodic agents, antimuscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutytin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), ZD-6169 (Zeneca Co., United Kingdom), and stilonium iodide.

In still another embodiment, the present intravesical drug delivery devices are used to treat infections involving the bladder, the prostate, the kidney, and the urethra. Antibiotics, antibacterial, antifungal, antiprotozoal, antiseptic, antiviral and other antiinfective agents can be administered for treatment of such infections. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In other embodiments, the drug delivery device is used to treat fibrosis of a genitourinary site, such as the bladder or uterus. Representative examples of drugs for the treatment of fibroids include pentoxphylline (xanthine analogue), anti-TNF, antiTGF agents, GnRH analogues, exogenous progestins, antiprogestins, selective estrogen receptor modulators, danazol and NSAIDs.

The implantable drug delivery devices also may be used to treat spastic or flaccid neurogenic bladder. Representative examples of drugs for the treatment of neurogenic bladder include analgesics or anaesthetics, such as lidocaine, bupivacaine, mepivacaine, prilocaine, articaine, and ropivacaine; anticholinergics; antimuscarinics such as oxybutynin or propiverine; a vanilloid, such as capsaicin or resiniferatoxin; antimuscarinics such as ones that act on the M3 muscarinic acetylcholine receptor (mAChRs); antispasmodics including $GABA_B$ agonists such as baclofen; botulinum toxins; capsaicins; alpha-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., Spinal Cord 42:267-72 (2004).

In one embodiment, the drug is selected from those known for the treatment of incontinence due to neurologic detrusor overactivity and/or low compliant detrusor. Examples of these types of drugs include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants); drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In another embodiment, the drug is selected from those known for the treatment of incontinence due to neurologic sphincter deficiency. Examples of these drugs include alpha adrenergic agonists, estrogens, beta-adrenergic agonists, tricyclic antidepressants (imipramine, amitriptyline). In still another embodiment, the drug is selected from those known for facilitating bladder emptying (e.g., alpha adrenergic antagonists (phentolamine) or cholinergics). In yet another embodiment, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., m3 muscarinc agonist, choline ester).

In certain embodiments, the drug is a steroid, such as triamcinolone, budesonide, or prednisolone. In certain embodiments, the drug is lidocaine, gemcitabine, docetaxel, carboplatin, cisplatin, oxaliplatin, trospium, tolterodine, oxybutynin, or mitomycin C.

Other Device Features

The devices described herein may include a radio-opaque portion or structure to facilitate detection or viewing (e.g., by X-ray imaging or fluoroscopy) of the device by a medical practitioner as part of the implantation or retrieval procedure. In one embodiment, the housing is constructed of a material that includes a radio-opaque filler material, such as barium sulfate or another radio-opaque material known in the art. Some housings may be made radio-opaque by blending radio-opaque fillers, such as barium sulfate or another suitable material, during the processing of the material from which the housing is formed. The radio-opaque material may be associated with the retention frame in those embodiments that include a retention frame. Ultrasound imaging or fluoroscopy may be used to image the device in vivo.

The drug delivery device may further include a retrieval feature, such as a string, a loop, or other structure that facilitates removal of the device from the body cavity, for example for removal of a non-resorbable device body following release of the drug formulation from the solid drug units. In one case, the device may be removed from the bladder by engaging the string to pull the device through the urethra. The device may be configured to assume a relatively narrow or linear shape when pulling the device by the retrieval feature into the lumen of a catheter or cystoscope or into the urethra.

Methods for Drug Delivery

The devices and methods disclosed herein may be adapted for use in humans, whether male or female, adult or child, or for use in animals, such as for veterinary or livestock applications. Accordingly, the term "patient" may refer to a human or other mammalian subject.

In certain embodiments, a method of administering a drug to a patient includes inserting a drug delivery device into a patient and permitting the drug to be released from the device. For example, the device may include any features, or combinations of features, described herein. In one embodiment, the drug is released from the drug reservoir lumen via diffusion through the second material of the second annular segment of the wall structure. In embodiments in which the wall structure comprises first and second wall structures, the method includes releasing the drug from the drug reservoir lumen via diffusion through the second wall structure.

In certain embodiments, permitting the drug to be released from the device includes permitting water to be imbibed through the water permeable wall portions or segments (e.g., through only the second wall structure/second material or through both the first and second wall structures/materials to solubilize the drug), and permitting the solubilized drug to be released from the device by diffusion through the second wall structure/material. That is, in certain embodiments, elution of drug from the device occurs following dissolution of the drug within the device. Bodily fluid enters the device, contacts the drug and solubilizes the drug, and thereafter the dissolved drug diffuses from the device. For example, the drug may be solubilized upon contact with urine in cases in which the device is implanted in the bladder. In one embodiment, releasing the drug from the device includes solubilizing the drug with water imbibed through the second wall structure/material, or both the first and second wall structures/materials.

In certain embodiments, the inserting comprises deploying the device through the patient's urethra and into the patient's urinary bladder. The device may be implanted non-surgically and may deliver drug for several days, weeks, months, or more after the implantation procedure has ended. In one embodiment, deploying the drug delivery device in the patient includes inserting the device into a body cavity or lumen of the patient via a deployment instrument. For example, the device may be deployed through a deployment instrument, such as a catheter or cystoscope, positioned in a natural lumen of the body, such as the urethra, or into a body cavity, such as the bladder. The deployment instrument typically is removed from the body lumen while the drug delivery device remains in the bladder or other body cavity for a prescribed treatment period.

The device, in some embodiments, may be deployed into the bladder of a patient in an independent procedure or in conjunction with another urological or other procedure or surgery, either before, during, or after the other procedure. The device may release one or more drugs that are delivered to local and/or regional tissues for therapy or prophylaxis, either peri-operatively, post-operatively, or both.

In one example, the device is deployed by passing the drug delivery device through a deployment instrument and releasing the device from the deployment instrument into the body. In cases in which the device is deployed into a body cavity such as the bladder, the device assumes a retention shape, such as an expanded or higher profile shape, once the device emerges from the deployment instrument into the cavity. The deployment instrument may be any suitable lumen device, such as a catheter, e.g., a urethral catheter, or cystoscope. These terms are used interchangeably herein, unless otherwise expressly indicated. The deployment instrument may be a commercially available device or a device specially adapted for the present drug delivery devices. In one embodiment, deploying the drug delivery device in the patient includes (i) elastically deforming the device into the relatively straightened shape; (ii) inserting the device through the patient's urethra; and (iii) releasing the device into the patient's bladder such that it assumes the coiled retention shape.

The drug delivery device may be passed through the deployment instrument, driven by a stylet or flow of lubricant or other fluid, for example, until the drug delivery device exits a lumen of the instrument as passes into the bladder. Thus, the device may be implanted into the bladder of a male or female human patient in need of treatment, either adult or child.

Once deployed in vivo, the device subsequently may release one or more drugs for the treatment of one or more conditions, locally to one or more tissues at the deployment site and/or regionally to other tissues distal from the deployment site. The release may be controlled and may release the drug in an effective amount over an extended period. Thereafter, the device may be removed, resorbed, excreted, or some combination thereof. In certain embodiments, the device resides in the bladder releasing the drug over a predetermined period, such as two weeks, three weeks, four weeks, a month, or more.

Once implanted, the device may provide extended, continuous, intermittent, or periodic release of a desired quantity of drug over a desired, predetermined period. In embodiments, the device can deliver the desired dose of drug over an extended period, such as 12 hours, 24 hours, 5 days, 7 days, 10 days, 14 days, or 20, 25, 30, 45, 60, or 90 days, or more. The rate of delivery and dosage of the drug can be selected depending upon the drug being delivered and the disease or condition being treated. In one embodiment, a rate of release of the drug from the drug delivery device is zero order over at least 36 hours. In one embodiment, a rate of the release of the drug from the drug delivery device is essentially zero order over at least 7 days.

The device may be used to treat interstitial cystitis, radiation cystitis, pelvic pain, bladder inflammation, overactive bladder syndrome, bladder cancer, neurogenic bladder, neuropathic or non-neuropathic bladder-sphincter dysfunction, infection, post-surgical pain or other diseases, disorders, and conditions treated with drugs delivered to the bladder. The device may release drug locally to the bladder and regionally to other sites near the bladder. The device may deliver drugs that improve bladder function, such as bladder capacity, compliance, and/or frequency of uninhibited contractions, that reduce pain and discomfort in the bladder or other nearby areas, or that have other effects, or combinations thereof. The bladder-deployed device also may deliver a therapeutically effective amount of one or more drugs to other genitourinary sites within the body, such as other locations within urological or reproductive systems of the body, including the kidneys, urethra, ureters, penis, testes, seminal vesicles, vas deferens, ejaculatory ducts, prostate, vagina, uterus, ovaries, or fallopian tubes, among others or combinations thereof. For example, the drug delivery device may be used in the treatment of kidney stones or fibrosis, erectile dysfunction, among other diseases, disorders, and conditions.

In one embodiment, the device may have two payloads of drug that are released at different times. The first payload may be adapted for relatively quick release, while the second payload may be adapted for more continuous release.

Subsequently, the device may be retrieved from the body, such as in cases in which the device is non-resorbable or otherwise needs to be removed. Retrieval devices for this purpose are known in the art or can be specially produced. The device also may be completely or partially bioerodible, resorbable, or biodegradable, such that retrieval is unnecessary, as either the entire device is resorbed or the device sufficiently degrades for expulsion, for example, from the bladder during urination. The device may not be retrieved or resorbed until some of the drug, or preferably most or all of the drug, has been released. If needed, a new drug-loaded device may subsequently be implanted, during the same procedure as the retrieval or at a later time.

Methods of Making the Device

The devices described herein generally are formed by using a co-extrusion process to form the elongated, elastic housing of the device; loading the drug reservoir lumen with a suitable quantity of the drug (optionally formulated with one or more excipients); and closing off the ends of the tubular housing.

In embodiments in which the drug permeable portion does not extend along the entire length of the elongated housing, the method of making the device includes forming the first annular segment by an extrusion process which comprises introducing the first material into an extrusion stream; and forming the second annular segment by intermittently introducing the second material into the extrusion stream with the first material at preselected positions, in a manner effective to form a tubular structure comprising one or more first annular segments integrally connected to one or more second annular segments. In particular, the first and second materials are located in the extrusion stream such that, in the second annular segment, the first material forms a first arcuate portion and the second material forms a second arcuate portion, wherein the first and second arcuate portions are integrally connected and together defining the annulus of the second annular segment. The method further includes cutting the tubular structure at one or more positions to form the elongated, elastic housing; loading a drug into the drug reservoir lumen; and sealing the first and second ends of the drug reservoir lumen. With this method, the resulting device may have a tubular wall structure as illustrated in FIGS. 8A-8D, FIGS. 9A-9B.

In another embodiment, the method of making the device includes forming the first annular segment by an extrusion process which comprises introducing the first material into an extrusion stream; and forming the second annular segment by intermittently introducing the second material into the extrusion stream to replace the first material along a selected length of the extrusion stream, in a manner effective to form a tubular structure comprising two or more first annular segments integrally connected to two or more second annular segments. In particular, the first annular segment is formed entirely of a first material which is impermeable to the drug, and the second annular segment is formed primarily of a second material which is permeable to the drug and configured to release the drug in vivo by diffusion through the second material. The term "primarily" is used to denote that any transition regions are, for purposed of description, included second annular segment. The method further includes cutting the tubular structure at one or more positions to form the elongated, elastic housing; loading a drug into the drug reservoir lumen; and sealing the first and second ends of the housing. With this method, the resulting device may have a tubular wall structure as illustrated in FIGS. 10A-10D.

In some embodiments, the tubular wall structure may include a retention lumen extending through the structure. The retention lumen optionally may be loaded with an elastic retention frame, such as a nitinol wire or other superelastic wire, and then sealed to keep the frame inside the lumen and/or optionally may be filled with a gas (e.g., air) and then sealed at its ends prior or subsequent to drug loading of the device. In another embodiment, the retention lumen may be filled with high durometer silicone, prior to drug loading of the device, which is then cured into a solid, elastic form effective to bias the tubular wall structure in the coiled bladder retention shape.

In other embodiments, the method includes thermally shape setting the tubular structure to have a coiled retention shape which is elastically deformable into an uncoiled shape. In such embodiments, a retention lumen and frame advantageously may not be necessary.

Some steps or sub-steps of the method of making a drug delivery device may be performed in other orders or simultaneously.

The present disclosure may be further understood with reference to the following non-limiting examples.

EXAMPLES

A study was performed to determine whether thermoplastic materials could be used to form a tubular drug housing that is thermally shaped to have a retention shape suited to retain the drug housing in the bladder and that is elastically deformable to a relatively straightened shape suited for insertion through a lumen into the bladder, without a retention frame or wire. A blended polymer material containing aliphatic polyether-based thermoplastic polyurethane Tecoflex™ (EG-80A) (Lubrizol Corp.) in an amount of 50 percent, by weight, and aliphatic, hydrophilic polyether-based thermoplastic polyurethane Tecophilic™ (HP-93A-100) (Lubrizol Corp.) in an amount of 50 percent, by weight, was formed into a tube having an inner diameter of about 2.16 mm and a wall thickness of about 0.81 mm.

A tube having a length of about 15 cm was bent and shaped thermally using a hot plate, heat gun, and wire fixture, to have a coiled, or pretzel-like, shape essentially consisting of two sub-circles, each having its own smaller arch and sharing a common larger arch. Then, Lactose tablets (diameter of about 2.16 mm) were inserted into in a length of about 13 cm and the ends of the tube were sealed by 2.77 mm (outer diameter) silicone spacers that were mechanically inserted into the ends.

Degassed deionized water (300 g) was poured into a beaker and the tube system was placed in the beaker, which then was placed in a 37° C. chamber with the top covered with parafilm.

Thus, it was concluded that a thermoplastic material (e.g., polyurethane blend) could be used to form a tubular drug housing that is thermally shaped to have a retention shape, in the absence of a retention frame or wire.

Another length of tubing was formed according to the above-described method, but was bent and shaped thermally using a hot plate, heat gun, and wire fixture, to have a multi-coil shape essentially consisting of four sub-circles, each having its own smaller arch and sharing a common larger arch with the adjacent sub-circle(s).

Many modifications and other implementations of the disclosure set forth herein will be apparent having the benefit of the teachings presented in the foregoing descriptions and the associated drawings. Therefore, it is to be understood that the disclosure is not to be limited to the specific implementations disclosed and that modifications and other implementations are intended to be included within the scope of the appended claims. Although specific terms are employed herein, they are used in a generic and descriptive sense only and not for purposes of limitation.

I claim:

1. A drug delivery device comprising:
an elongated, elastic housing having a drug reservoir lumen extending between a first closed end and a second closed end; and
a drug contained in the drug reservoir lumen,
wherein:
the housing comprises a tubular wall structure which comprises:
a first annular segment formed entirely of a first material which is impermeable to the drug, and
a second annular segment formed at least partially of a second material which is permeable to the drug and configured to release the drug in vivo by diffusion through the second material in the second annular segment, and
the first annular segment has a first end which is integrally formed and connected with a first end of the second annular segment.

2. The device of claim 1, wherein the second annular segment is formed of the first material and the second material.

3. The device of claim 2, wherein in the second annular segment, the first material forms a first arcuate portion and the second material forms a second arcuate portion, the first and second arcuate portions being integrally connected and together defining the annulus of the second annular segment.

4. The device of claim 3, wherein the second arcuate portion has an arc angle from 15 degrees to 120 degrees.

5. The device of claim 3, wherein the second arcuate portion has an arc angle from 30 degrees and 60 degrees.

6. The device of claim 1, wherein the second annular segment is formed primarily of the second material.

7. The device of claim 1, wherein the first and second annular segments are formed together in an extrusion process.

8. The device of claim 1, wherein the tubular wall structure further comprises a third annular segment which is formed entirely of the first material and which is integrally formed and connected with an opposed second end of the second annular segment.

9. The device of claim 8, wherein the second and third annular segments are formed together in the extrusion process.

10. The device of claim 1, wherein the tubular wall structure has a total length ($L_T$) between opposed ends of the housing and the second annular segment has a length (L) which is from 5% to 50% of the total length ($L_T$).

11. The device of claim 1, wherein the first material comprises silicone, thermoplastic polyurethane, or ethylene-vinyl acetate (EVA).

12. The device of claim 1, wherein the second material comprises a hydrophilic thermoplastic polyurethane.

13. The device of claim 1, wherein the device is configured to be elastically deformable from a coiled retention shape suited to retain the device within the urinary bladder of a patient to an uncoiled shape suited for insertion through the patient's urethra and into the bladder, in the absence of a wire retention frame.

14. The device of claim 1, wherein the drug is in the form of a plurality of solid tablets.

15. A drug delivery device comprising:
a tubular housing having a closed drug reservoir lumen bounded by a wall structure comprising at least one thermoplastic material; and
a drug contained in the drug reservoir lumen,
wherein:
at least a portion of the wall structure is water permeable,
at least a portion of the wall structure is permeable to the drug such that the drug is releasable in vivo by diffusion through the drug permeable portion of the wall structure,
the tubular housing is thermally shape set to have a coiled retention shape suited to retain the device within the urinary bladder of a patient and is elastically deformable from the coiled retention shape to an uncoiled shape suited for insertion of the device through the patient's urethra and into the bladder, and
the wall structure comprises: (i) a first annular segment formed entirely of a first material which is impermeable to the drug, and (ii) a second annular segment formed at least partially of a second material which is permeable to the drug and configured to release the drug in vivo by diffusion through the second material in the second annular segment, wherein the first annular segment has a first end which is integrally formed and connected with a first end of the second annular segment.

16. The device of claim 15, wherein the first material comprises a first thermoplastic polyurethane composition and the second material comprises a second thermoplastic polyurethane composition which is different from the first thermoplastic polyurethane composition.

17. The device of claim 15, wherein the first and second wall structures are integrally formed in a coextrusion process.

18. The device of claim 15, wherein the coiled retention shape comprises at least one loop having a radius of curvature of at least 0.5 cm.

19. The device of claim 15, wherein the drug is in the form of a plurality of solid tablets.

20. A method of administering a drug to a patient in need thereof, comprising:
inserting into the patient the device of claim 1;
permitting water to be imbibed through the tubular wall structure to solubilize the drug; and
permitting the solubilized drug to be released from the device by diffusion through the second annular segment of the tubular wall structure.

* * * * *